US011532406B2

(12) United States Patent
DeGrado et al.

(10) Patent No.: US 11,532,406 B2
(45) Date of Patent: Dec. 20, 2022

(54) HIGH SPECIFIC ACTIVITY PREPARATION OF F-18 TETRAFLUOROBORATE

(71) Applicant: Mayo Foundation for Medical Education and Research, Rochester, MN (US)

(72) Inventors: Timothy R. DeGrado, Rochester, MN (US); Huailei Jiang, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 924 days.

(21) Appl. No.: 16/095,865

(22) PCT Filed: Apr. 24, 2017

(86) PCT No.: PCT/US2017/029089
§ 371 (c)(1),
(2) Date: Oct. 23, 2018

(87) PCT Pub. No.: WO2017/189415
PCT Pub. Date: Nov. 2, 2017

(65) Prior Publication Data
US 2021/0225547 A1 Jul. 22, 2021

Related U.S. Application Data

(60) Provisional application No. 62/327,134, filed on Apr. 25, 2016.

(51) Int. Cl.
*A61K 51/02* (2006.01)
*C01B 35/06* (2006.01)
*G21G 4/08* (2006.01)
*B01J 41/05* (2017.01)

(52) U.S. Cl.
CPC ............ *G21G 4/08* (2013.01); *A61K 51/025* (2013.01); *B01J 41/05* (2017.01); *C01B 35/063* (2013.01)

(58) Field of Classification Search
CPC ............ A61K 2123/00; A61K 2121/00; A61K 51/00; A61K 51/025; G21G 4/08; B01J 41/05; B01J 47/022; B01J 49/57; B01J 49/60; C01B 35/063
USPC ..... 424/1.11, 1.65, 1.81, 1.85, 1.89, 9.1, 9.2
See application file for complete search history.

(56) References Cited

U.S. PATENT DOCUMENTS

| | | | |
|---|---|---|---|
| 9,988,336 B2 * | 6/2018 | Degrado | ............ A61K 51/02 |
| 2011/0006011 A1 | 1/2011 | Aerts et al. | |
| 2012/0082608 A1 | 4/2012 | Waki et al. | |
| 2014/0039074 A1 | 2/2014 | Chi et al. | |

OTHER PUBLICATIONS

Youn et al, Eur. J. Nucl. Mol. Imaging, vol. 37, pp. 2105-2107 (Year: 2010).*
Jiang et al, The Journal of Nuclear Medicine, published online Apr. 21, 2016, vol. 57, Nol. 9, pp. 1454-14592016 (Year: 2016).*
International Search Report and Written Opinion from Parent PCT/US2017/29089, dated Jul. 21, 2017, 12 pages.
Jiang, et al. Synthesis of 18F-Tetrafluoroborate via Radiofluorination of Boron Trifluoride and Evaluation in a Murine C6-Glioma Tumor Model, Apr. 21, 2016, The Journal of Nuclear Medicine, vol. 57, No. 9, pp. 1454-1459.
Ahn, Sodium Iodide Symporter for Nuclear Molecular Imaging and Gene Therapy: From Bedside to Bench and Back, Theranostics, 2012, 2(4):392-402.
Anbar et al., Effect of Monofluorosulphonate, Difluorophosphate and Fluoroborate Ions on the Iodine Uptake of the Thyroid Gland, Nature, 1959, 183(4674):1517-1518.
Anbar et al., The Accumulation of Fluoroborate Ions in Thyroid Glands of Rats, Endocrinology, 1960, 66:888-890.
Anbar et al., The Isotopic Exchange of Fluoroboric Acid with Hydrofluoric Acid, Journal of Physical Chemistry, 1960, 64(12):1896-1899.
Burke et al., Boron-18F Containing Positron Emission Tomography Radiotracers: Advances and Opportunities, Contrast Media & Molecular Imaging, 2015, 10(2):96-110.
Cai et al., Chemistry with [18F]Fluoride Ion, European Journal of Organic Chemistry, 2008, 17:2853-2873.
Chung, Sodium Iodide Symporter: Its Role in Nuclear Medicine, Journal of Nuclear Medicine, 2002, 43(9):1188-1200.
Dai et al., Cloning and Characterization of the Thyroid Iodide Transporter, Nature, 1996, 379(6564):458-460.
Daniels et al., Will Radioiodine Be Useful in Treatment of Breast Cancer?, Nature Medicine, 2000, 6(8):859-860.
Eskandari et al., Thyroid Na+/I—Symporter Mechanism, Stoichiometry, and Specificity, Journal of Biological Chemistry, 1997, 272(43):27230-27238.
Groot-Wassink et al., Quantitative Imaging of Na/I Symporter Transgene Expression Using Positron Emission Tomography in the Living Animal, Molecular Therapy, 2004, 9(3):436-442.
Jauregoi-Orsoro et al. Synthesis and Biological Evaluation of [18 F] tetrafluoroborate: a PET Imaging Agent for Thyroid Disease and Reporter Gene Imaging of the Sodium/Iodide Symporter, European Journal of Nuclear Medicine and Molecular Imaging, 2010, 37(11):2108-2116.
Khoshnevisan et al., [18 F] Tetrafluoroborate as a PET Tracer for the Sodium/Iodide Symporter: The Importance of Specific Activity, EJNMMI Research, 2016, 6(1):1-10.
Liu et al., Rapid, One-Step, High Yielding 18F-Labeling of an Aryltrifluoroborate Bioconjugate by Isotope Exchange at Very High Specific Activity, Journal of Labelled Compounds and Radiopharmaceuticals, 2012, 55(14):491-496.

(Continued)

*Primary Examiner* — D. L. Jones
(74) *Attorney, Agent, or Firm* — Quarles & Brady LLP

(57) ABSTRACT

Embodiments of the invention provide methods of synthesizing $^{18}$F-tetrafluoroborate ($^{18}$F-TFB) via direct radiofluorination on boron trifluoride ($BF_3$) to enhance both labeling yield and specific activity. Uses of $^{18}$F-TFB are also contemplated.

9 Claims, 16 Drawing Sheets

(56) References Cited

OTHER PUBLICATIONS

Penheiter et al., The Sodium Iodide Symporter (NIS) as an Imaging Reporter for Gene, Viral, and Cell-Based Therapies, Current Gene Therapy, 2012, 12(1):33-47.
Ryo et al., Thyroid Imaging Agents: A Comparison of I-123 and Tc-99m Pertechnetate, Radiology, 1983, 148(3):819-822.
Schmitz, The Production of [124 I] Iodine and [86 Y] Yttrium, European Journal of Nuclear Medicine and Molecular Imaging, 2011, 38(Suppl 1):S4-S9.
Sparagana et al., Rapid Evaluation of Thyroid Nodules Using 99mTc-Pertechnetate Scanning, Journal of Nuclear Medicine, 1970, 11(5):224-225.
Wamser, Hydrolysis of Fluoboric Acid in Aqueous Solution, Journal of the American Chemical Society, 1948, 70(3):1209-1215.
Wamser, Equilibria in the System Boron Trifluoride—Water at 25 Degrees, Journal of the American Chemical Society, 1951, 73(1):409-416.
Weeks, Evaluation of [18F]-tetrafluoroborate as a Potential PET Imaging Agent for the Human Sodium/Iodide Symporter in a New Colon Carcinoma Cell Line HCT116 Expressing hNIS, Nuclear Medicine Communications, 2011, 32(2):98-105.
Youn et al., A New PET Probe, 18 F-tetrafluoroborate, for the Sodium/Iodide Symporter: Possible Impacts on Nuclear Medicine, European Journal of Nuclear Medicine and Molecular Imaging, 2010, 37(11):2105-2107.
European Patent Office, Extended European Search Report, Application No. 17790181.6, dated Nov. 26, 2019, 9 pages.

\* cited by examiner

HIGH SPECIFIC ACTIVITY PREPARATION OF F-18 TETRAFLUOROBORATE

CROSS-REFERENCES TO RELATED APPLICATIONS

This application is a 371 application of PCT/US2017/029089, filed Apr. 24, 2017, which claims priority to U.S. Provisional Application No. 62/327,134 entitled "High Specific Activity Preparation of F-18 Tetrafluoroborate" filed on Apr. 25, 2016, each of which is incorporated by reference in its entirety.

STATEMENT REGARDING FEDERALLY SPONSORED RESEARCH

Not Applicable.

BACKGROUND

The sodium/iodide symporter (NIS) is an intrinsic membrane glycoprotein, which mediates the uptake of iodide in the thyroid gland and other NIS expressing cells or tissues [1-3]. The active transport of iodide is the basis for the diagnosis and therapeutic treatment of thyroid disease and thyroid cancer. The clinical application of radioiodine also builds the foundation of modern nuclear medicine [4]. The identification and characterization of human NIS (hNIS) in 1996 [5, 6] created new opportunities for the use of hNIS as a reporter gene in viral therapy investigations and imaging of cell migration and differentiation. Despite considerable success in single photon imaging of the thyroid and thyroid cancers with $^{123}$I, $^{131}$I, or [$^{99m}$Tc]pertechnetate [2, 3], there remain obvious limitations for use of these radioisotopes for diagnostic imaging. Both $^{123}$I ($T_{1/2}$=13.13 h) and $^{131}$I ($T_{1/2}$=8.02 d) are true iodine imaging radiotracers, but have longer half lives than required for a diagnostic study, which result in unnecessarily high dose of irradiation to patients and staff. [$^{99m}$Tc]pertechnetate ($T_{1/2}$=6 h) has found use as a radioiodine analog in thyroid diseases [7, 8], and has suitable properties for single photon emission computed tomography (SPECT). Nevertheless, SPECT has the limited resolution and sensitivity, especially in detection of small metastases and low volume diseases. Positron emission tomography (PET) has significantly better sensitivity and quantitative accuracy than SPECT, particularly for accumulations in small regions. The positron emitter $^{124}$I ($T_{1/2}$=4.2 d) has been used in NIS imaging [9].

However, the unnecessarily long half-life of $^{124}$I and its complex emission properties that include high energy gamma photons are drawbacks for diagnostic imaging applications. Also, the production of $^{124}$I requires specialized solid target systems which are not available in most cyclotron facilities [10]. Positron emitting $^{18}$F-fluoride ([$^{18}$F], $T_{1/2}$=109.7 min) is the most commonly employed radioisotope for PET imaging. It has favorable physical decay properties of 97% positron emission and low positron energy ($\beta+_{max}$=0.635 MeV) and is produced by all PET cyclotrons. The development of $^{18}$F-fluoride based PET tracers for NIS imaging would be encouraging. Since various anions (e.g., I$^-$, SeCN$^-$, SCN$^-$, ReO$_4^-$, TcO$_4^-$, NO$_3^-$) are transported by NIS [6], the critical physicochemical features of these well transported substrates is anionic monovalency with similar size and space-filling properties as the iodide ion. Before the advent of clinical PET, in 1950s and early 1960s, Anbar et al. [11, 12] reported that the tetrafluoroborate (TFB, BF$_4^-$) anion was effective to inhibit thyroid uptake of iodide ion. These researchers also showed that [$^{18}$F] labeled TFB, synthesized from reactor produced $^{18}$F-fluoride, specifically accumulated in rat thyroid. The initial labeling of TFB was accomplished by an ion exchange reaction of KBF$_4$ in acid at room temperature or heating to make $^{18}$F-TFB, and the potassium salt was purified by recrystallization after neutralization [13]. The isotopic exchange labeling approach inherently results in low specific activity $^{18}$F-TFB. Recently, Jauregui-Osoro et al. [14] updated the labeling of $^{18}$F-TFB using current $^{18}$F-fluoride production and purification methods. With the same mechanism, $^{18}$F-TFB was synthesized in mixture of 1 mg NaBF$_4$ and 1.5 N HCl at 120° C. After filtration through a Dionex AG cartridge (a cation exchange cartridge loaded with silver ions) and alumina cartridge, $^{18}$F-TFB of >96% radiochemical purity was obtained in approximately 10% yield. The specific activity was ~1 GBq/μmol with starting activities of 12-18 GBq of $^{18}$F-fluoride [14]. PET/CT imaging in normal mice with transgenic thyroid tumors showed $^{18}$F-TFB to delineate uptake in normal tissues expressing NIS (thyroid, stomach, salivary glands) and enhanced uptake in thyroid tumor. Researchers from the same institution also showed that $^{18}$F-TFB was effective as a NIS probe in the NIS-transfected colon carcinoma cell line, HCT116 [15]. However, as pointed out by Youn et al. [16], specific activities achieved by the reported method are substantially lower than those typically required for receptor-mediated radiopharmaceuticals (~30 GBq/mmol). Therefore, there is a need for synthesis of $^{18}$F-TFB with higher specific activity.

SUMMARY OF THE INVENTION

The present disclosure describes in one aspect a method of radiolabeling tetrafluoroborate (TFB) with $^{18}$F-fluoride, the method comprising direct radiofluorination on boron trifluoride (BF$_3$) by reacting the BF$_3$ directly with $^{18}$F-fluoride.

In another aspect the present disclosure provides a method of radiolabeling tetrafluoroborate with $^{18}$F-fluoride, the method comprising: (a) reacting $^{18}$F-fluoride with BF$_3$; and (b) isolating the $^{18}$F-TFB from unreacted $^{18}$F-fluoride and BF$_3$. In some aspects, the $^{18}$F-fluoride is trapped on an anion exchange cartridge and the reacting of step (a) of $^{18}$F-fluoride with BF$_3$ is performed on the anion exchange cartridge.

In another aspect, the method of radiolabeling tetrafluoroborate with [$^{18}$F]fluoride, the method consisting essentially of: (a) trapping $^{18}$F-fluoride on an anion exchange column; (b) reacting [$^{18}$F]fluoride with BF$_3$; and (c) isolating the $^{18}$F-TFB from unreacted $^{18}$F-fluoride and BF$_3$ from the anion exchange column, wherein the resultant $^{18}$F-TFB has a specific activity of at least 5 GBq/μmol.

In another aspect, a high specific activity preparation of $^{18}$F-tetrafluoroborate is provided. The high specific activity preparation is prepared by the methods disclosed herein. In some aspects, the preparation has at least 95% radiochemical purity. In some aspects, the specific activity is at least 8 GBq/μmol.

In yet another aspect, methods of use of the high specific activity preparation of $^{18}$F-tetrafluoroborate are provided. Suitable uses include, for example, imaging the thyroid, breast, stomach, salivary glands or kidneys of a subject. Other suitable uses include imaging of thyroid or breast cancer in a subject. Another suitable use is for monitoring gene therapies that employ the hNIS reporter gene.

These and other features, aspects, and advantages of the present invention will become better understood upon consideration of the following detailed description, drawings, and appended claims.

DETAILED DESCRIPTION

Figure 1A:
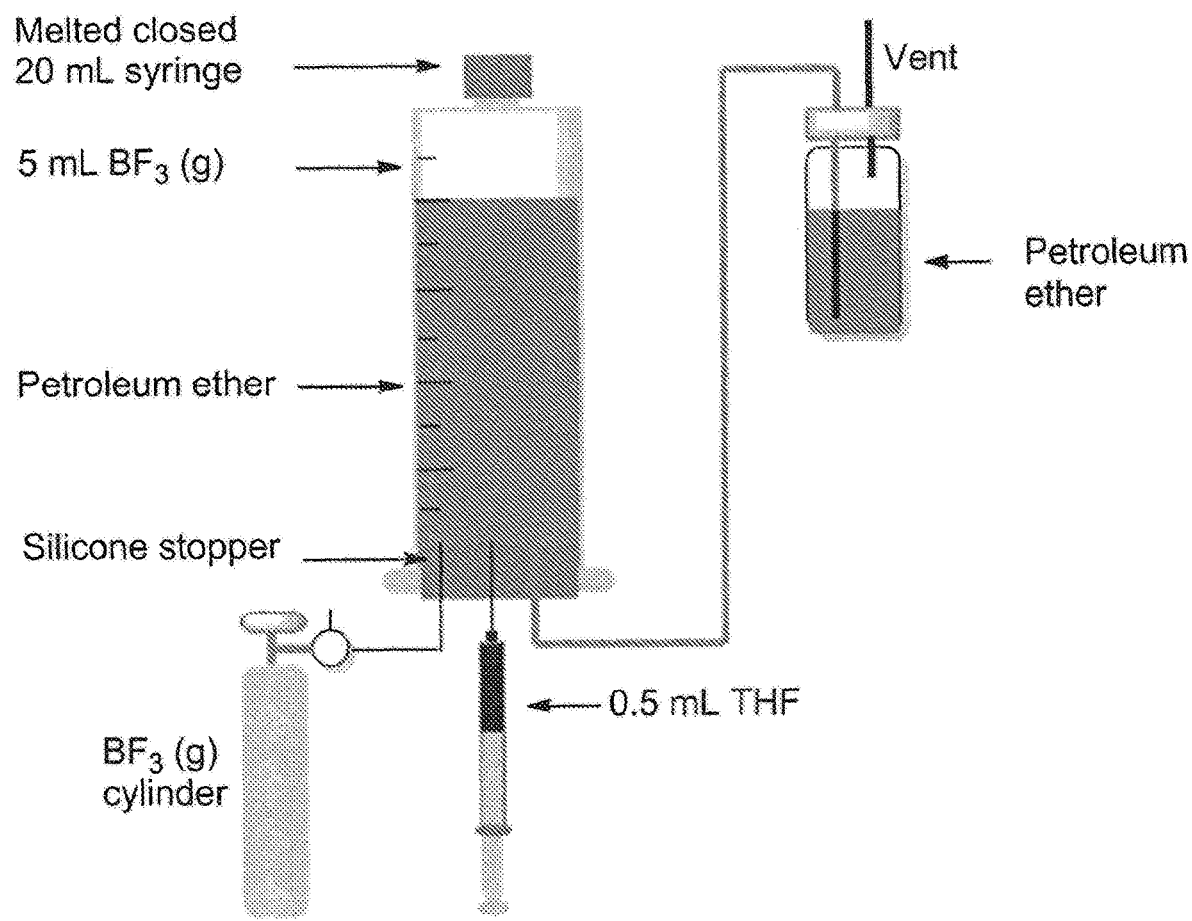
FIG. 1A is a schematic showing the preparation of $BF_3$.THF/PE complex solution.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The following discussion is presented to enable a person skilled in the art to make and use embodiments of the invention. Various modifications to the illustrated embodiments will be readily apparent to those skilled in the art, and the generic principles herein can be applied to 7other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

A method of radiolabeling tetrafluoroborate (TFB) with $^{18}$F-fluoride is provided. The method comprises the direct radiofluorination on boron trifluoride ($BF_3$) by reacting the $BF_3$ directly with $^{18}$F-fluoride. This method provides $^{18}$F-TFB with an enhanced labeling yield and higher specific activity.

In some embodiments, the method comprises (a) reacting $^{18}$F-fluoride with $BF_3$; and (b) isolating the $^{18}$F-TFB from unreacted $^{18}$F-fluoride and $BF_3$. In some embodiments, the $^{18}$F-fluoride is trapped on an anion exchange cartridge or column and the reacting of step (a) of $^{18}$F-fluoride with BF$_3$ is performed on the anion exchange cartridge or column. In this method, the reacted $^{18}$F-TFB remains on the anion exchange cartridge or column to be separated from the unreacted $^{18}$F-fluoride and BF$_3$.

Suitable anion exchange columns or cartridges are known in the art. For example, in some embodiments, the anion exchange cartridge is a quaternary methyl ammonium anion exchange (QMA) cartridge. Suitable anion exchange resins will have a sufficient affinity for $^{18}$F-TFB as to be able to separate the $^{18}$F-TFB from the unreacted $^{18}$F-fluoride and BF$_3$.

In some embodiments, the anion exchange cartridge or column containing the $^{18}$F-TFB is washed at least once to remove the unreacted BF$_3$ and residual solvent from the cartridge. The anion exchange cartridge or column may be washed with a suitable wash solution. Suitable wash solutions include, but not limited to, for example, THF and/or water to remove the unreacted BF$_3$ and residual solvent. In some embodiments, the wash solution comprises ether. In some embodiments, the cartridge or column is washed at least one, at least twice, at least three times. In some embodiments, the column is first washed with THF and then washed with distilled water. In another embodiment, the column is washed sequentially with THF and water. In some embodiments, the column is washed with about 10 mL of THF followed by 10 mL of water.

The $^{18}$F-TFB is eluted from the anion exchange column. In some embodiments, the $^{18}$F-TFB is eluted using saline. In other embodiments, the $^{18}$F-TFB is eluted with solution selected from the group consisting of phosphate buffer saline (PBS), sodium citrate, sodium chloride and sodium bicarbonate. Suitable concentrations of saline for removal of the $^{18}$F-TFB are known in the art and include, but are not limited to, about 0.9% NaCl.

The eluted crude $^{18}$F-TFB may be further purified by passing through a second column or cartridge comprising alumina with a neutral surface chemistry. Suitable columns or cartridges include, but are not limited to, for example, alumina-N SepPak Plus cartridge (SepPak®). The second column or cartridge is used to remove unreacted $^{18}$F-fluoride from the solution. The eluted crude $^{18}$F-TFB may be passed over at least one second column or cartridge. In some embodiments, the eluted crude $^{18}$F-TFB may be passed over at least two second column or cartridges. In some embodiments, the eluted crude $^{18}$F-TFB may be passed over at least three second column or cartridges. In some embodiments, the eluted $^{18}$F-TFB is passage through a sterilizing filter. In some embodiments, the sterilizing filter is 0.2 μM.

For the methods provided herewith, BF$_3$ may be provided in a solution of BF$_3$.THF complex in petroleum ether. BF$_3$.THF may be produced by methods known in the art, for example, from BF$_3$ gas dissolved in THF using petroleum ether. In some instances, the BF$_3$.THF complex was filtered to remove BF$_4$— before reacting with $^{18}$F-fluoride. In some embodiments, the BF$_3$.THF complex was passed over a anion exchange resin, for example, an anion exchange resin that contains crosslinked polystyrene matrix with tertiary amine and quaternary ammonium functional groups (e.g. Lewatit® MP-64).

In other embodiments, the BF$_3$ may be provided as, for example, BF$_3$.pyridine, BF$_3$.Et$_3$N, BF$_3$.MeOH, BF$_3$.EtOH, BF$_3$.Et$_2$O and BF$_3$.THF, among others. [The $^{18}$F-fluoride may be prepared by known methods in the art, for example, by irradiation of $^{18}$O-water. Suitable methods of irradiating $^{18}$O-water are known in the art, and include, using 50-70 uA (e.g. 65 uA) for about 10-30 (e.g. 15) minutes in cyclotron.

In some embodiments, the $^{18}$F-fluoride used has radioactivities of about 10 to about 50 MBq. In some embodiments, the $^{18}$F-fluoride used has radioactivities of about 15 to about 37 MBq.

The disclosed methods provide purified $^{18}$F-TFB with of specific activity of at least 5 GBq/μmol. In some instances, the methods provide $^{18}$F-TFB with a specific activity of at least 8 GBq/μmol. In one embodiment, the purified $^{18}$F-TFB has a specific activity of at least 8.8 GBq/μmol.

The disclosed methods synthesize $^{18}$F-TFB with a radiochemical yield of at least 15% with greater than about 95% purity. In some embodiments, methods provide $^{18}$F-TFB with a radiochemical yield of up to 40% with greater than about 95% purity. In some instances, the radiochemical yield is at least about 10%, at least about 20%, at least about 30%, at least about 40%.

The disclosure provides $^{18}$F-TFB made by the methods provided. The $^{18}$F-TFB is at least about 95% pure, in some embodiments, at least 98% pure. In some embodiments, the methods synthesize $^{18}$F-TFB with at least about 95% purity. In some embodiments, the methods synthesize $^{18}$F-TFB with about 98% purity. The $^{18}$F-TFB provide has a specific activity of at least 3 GBq/μmol, alternatively at least 5 GBq/μmol, alternatively at least 8 GBq/μmol.

In some embodiments, a method of radiolabeling tetrafluoroborate with $^{18}$F-fluoride consists essentially of: (a) trapping $^{18}$F-fluoride on an anion exchange column; (b) reacting $^{18}$F-fluoride with BF$_3$; and (c) isolating the $^{18}$F-TFB from unreacted $^{18}$F-fluoride and BF$_3$ from the anion exchange column, wherein the resultant $^{18}$F-TFB has a specific activity of at least 5 GBq/μmol. In this method, the $^{18}$F-TFB remains attached to the column or cartridge until eluted using an isotonic saline solution. The column or cartridge containing $^{18}$F-TFB may be washed with at least one wash solution before eluting the $^{18}$F-TFB. The method may further include purifying the $^{18}$F-TFB by running over a column or cartridge comprising alumina with a neutral surface chemistry. Suitable columns or cartridges include, but are not limited to, for example, alumina-N SepPak® Plus cartridge (SepPak®). In some embodiments, the eluted $^{18}$F-TFB is passage through a sterilizing filter.

This disclosure provides methods of synthesizing $^{18}$F-TFB in less than 30 minutes, alternatively less than 20 minutes, alternatively less than 10 minutes. In one embodiment, the method of synthesizing $^{18}$F-TFB is performed in about 10 minutes, in some instances in about 9 to 15 minutes. The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1: Synthesis of $^{18}$F-Tetrafluoroborate ($^{18}$F-TFB) Via Radiofluorination of Boron Trifluoride and Evaluation in Murine C6-Glioma Tumor Model Materials and Methods Lewatit® MP-64 chloride form resin was procured from Sigma Aldrich (St. Louis, Mo.) and preconditioned with 1 M $K_2CO_3$ solution (10 equivalent), water (100 equivalent, w/w) and tetrahydrofuran (THF) (100 equivalent, w/w) in a column, and then dried under nitrogen overnight. Acetone, THF and a $BF_3$ gas cylinder were purchased from Sigma Aldrich. Petroleum ether was procured from Fisher Scientific. Sep-Pak Accell Plus QMA Carbonate Plus Light (46 mg sorbent per cartridge, 40 μm particle size), Alumina-N SepPak Plus cartridges and Alumina-N SepPak Light cartridges were obtained from Waters Corporation (Waltham, Mass.). A Mini-scan radio-TLC scanner from Bioscan, Inc was used to monitor the radiochemical purity. Anion chromatography HPLC (Dionex IC-2100, AS19 analytical column 4.7×150 mm, eluent 35 mM KOH, sample volume 25 uL, flow rate 1 mL/min) was calibrated to measure $^{18}$F-TFB and $^{18}$F-TFB concentrations with conductivity and radioactivity detectors in series. The method was validated by separation of a series of anions ($F^-$, $Cl^-$, $Br^-$, $I^-$, $NO_3^-$, $CO_3^{2-}$, and $BF_4^-$) and $OH^-$ was negated by the system, Residual organic solvents were analyzed by GC (helium carrier gas flow at 10 cc/min through a MXTWAX column (Restek, Bellefonte, Pa., 0.53 mm ID, 30 m length)). The temperature program was 4 min at 35° C., followed by a temperature ramp of 4° C. per min to a maximum of 150° C.

Preparation of $BF_3$.THF Complex Solution

Figure 1B:
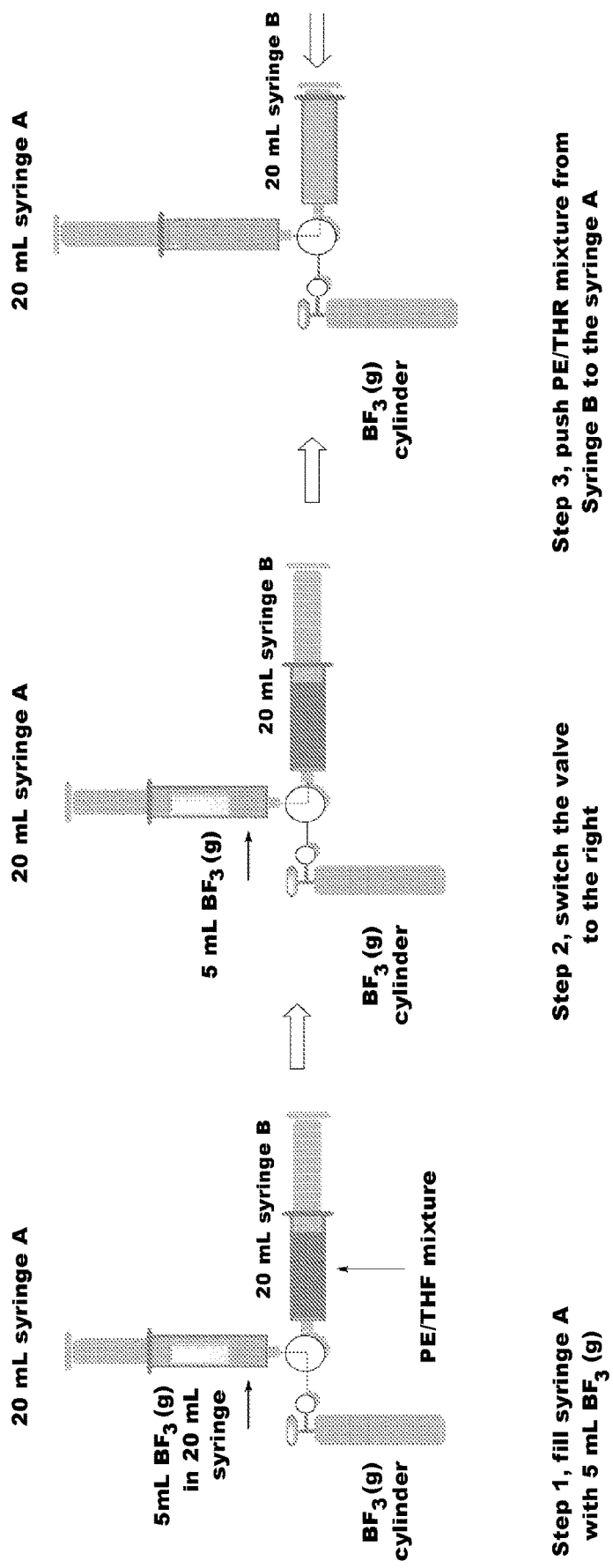
FIG. 1B is a schematic of an alternative simplified method of preparing $BF_3$.THF/PE complex solution.
Figure 2:
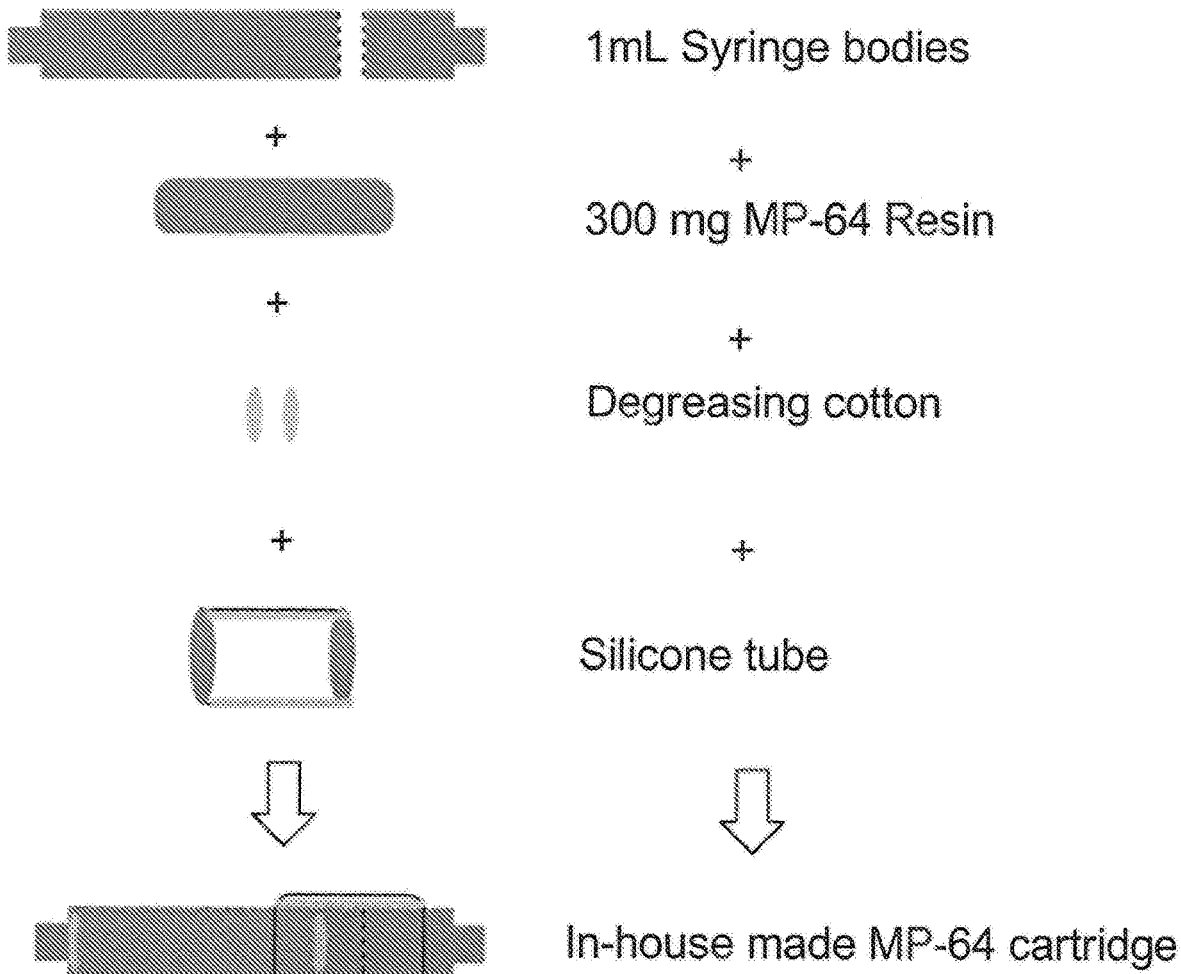
FIG. 2 is a depiction of the in-house-made Lewatit® MP-64 cartridge.

A solution of $BF_3$.THF complex in petroleum ether was prepared freshly within 30 min of the radiosynthesis of $^{18}$F-TFB (FIG. 1A). The luer opening of a 20 mL polypropylene syringe was melted closed. A silicone stopper was placed in the opposite opening. A 20 mL sterile vial with PEEK tubing was connected to the 20 mL syringe as shown in FIG. 1. The syringe body was completely filled with petroleum ether and about half of the sterile vial was also filled with petroleum ether (PE). $BF_3$ gas (~5 mL) was flowed into the syringe from a $BF_3$ cylinder through a PEEK tube, thereby displacing the corresponding petroleum ether to the sterile vial. After removal of the $BF_3$ addition tube, 0.5 mL THF was injected through the silicone stopper. The $BF_3$ gas was dissolved in the added THF quickly, and petroleum ether was sucked back into the syringe from the auxiliary vial without entry of atmospheric air. The tube was removed and the mixture became a homogenous solution with gentle shaking. The concentration of the $BF_3$ in the solution was ~1.8 μmol/mL. (FIG. 1A) FIG. 1B shows an alternative method using a simple manifold/syringe system. As shown in FIG. 1B, Step 1 you fill the syringe A with 5 ml $BF_3$ and Syringe B with PE/THF mixture; step 2 you switch the valve to the right and step 3 you push PE/THF mixture from Syringe B to the syringe A. Preparation of in-house-made Lewatit MP-64 cartridge A 1 mL syringe body was filled with 300 mg Lewatit® MP-64 (carbonate form) and stoppered with some degreasing cotton at both sides. The syringe was cut off and jointed with another 1 mL syringe body using a sheath of silicone tubing (FIG. 2).

[$^{18}$F]TFB Synthesis Method

Figure 3:
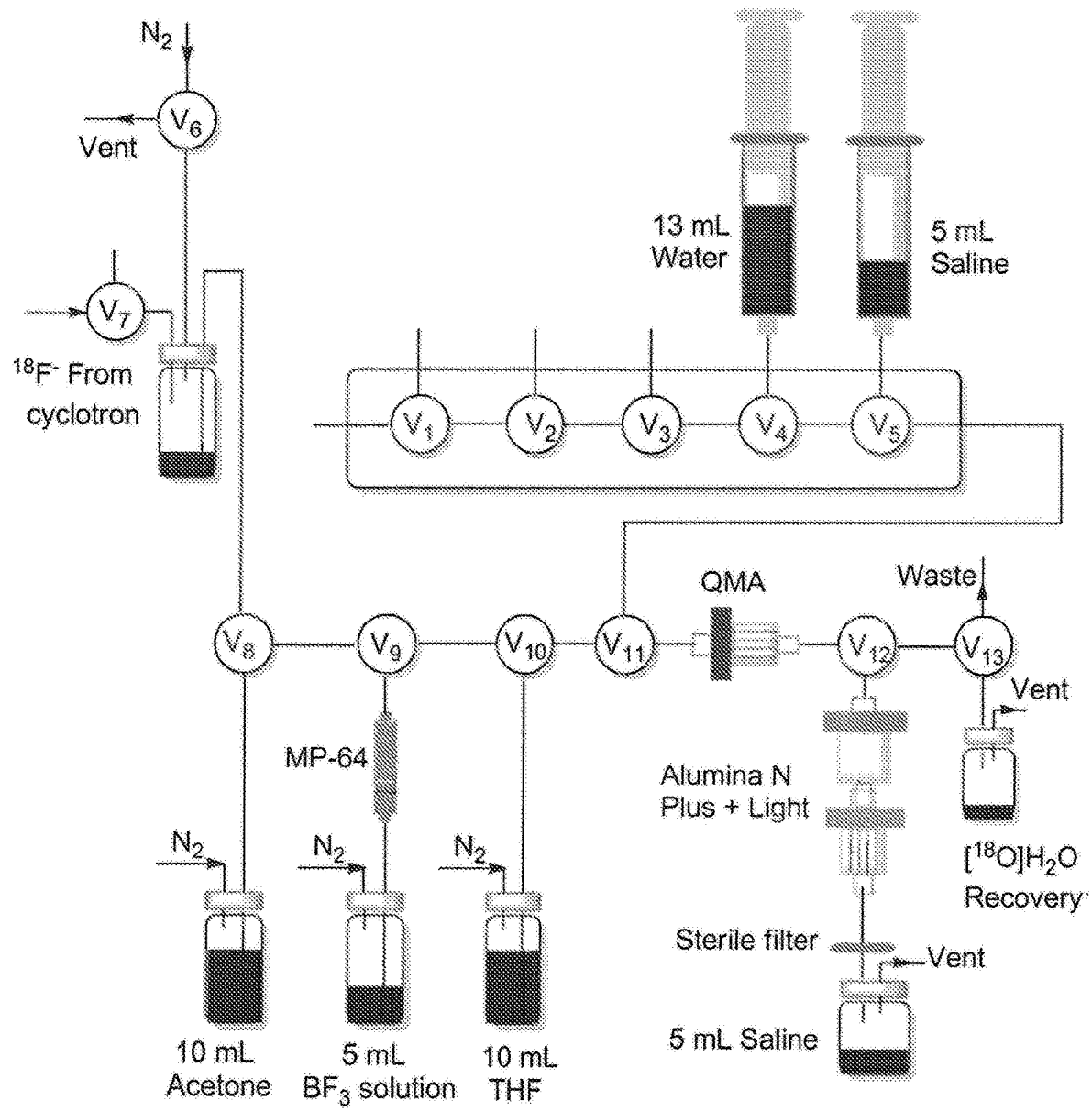
FIG. 3 is a schematic of automated module for the preparation of $^{18}$F-TFB. Valves V1-V5 are composed of a single-use cassette that is mounted to the front of the module. All other valves are non-disposable Teflon diaphragm solenoid valves.

An automated synthesis of $^{18}$F-TFB was developed for the preparation of $^{18}$F-TFB (FIG. 3). $^{18}$F-fluoride (37.6-40.5 GBq) was made by irradiation of 2.5 mL [$^{18}$O]water with 65 uA for 15 min in GE PETtrace cyclotron, and then delivered to the hot cell and trapped on a QMA (46 mg, carbonate form) cartridge. $^{18}$O-enriched water was collected using valve V13. The QMA cartridge was rinsed with 10 mL anhydrous acetone, and flushed with nitrogen for 100 seconds. The freshly prepared $BF_4$.THF complex solution (5 mL) was filtered by an in-house-made Lewatit® MP-64 cartridge (200400 mg), and then passed through the QMA cartridge within 10 s to react with the trapped $^{18}$F-fluoride to form $^{18}$F-TFB. The QMA cartridge was rinsed with a solution of 10 mL THF, flushed for 100 s with nitrogen, and rinsed with 13 mL water to further remove impurities. The QMA was then treated with 5 mL sterile 0.9% NaCl, USP solution (saline) to elute into a product vial pre-loaded with an additional 5 mL saline.

The crude $^{18}$F-TFB product solution was further purified from unreacted $^{18}$F-fluoride by passing three alumina-N SepPak Light cartridges before passage through a 0.2 μM sterilizing filter with final collection of the $^{18}$F-TFB in a product vial. (FIG. 3)

Quality Control

The product $^{18}$F-TFB was analyzed for radiochemical purity by both radio-TLC (MeOH, Rf=0.8-0.85) and anion chromatography HPLC with radioactivity detector (Dionex IC-2100, AS19 analytical column: 4.7×150 mm; eluent: 35 mM KOH; sample volume: 25.L; flow rate: 1 mL/min; retention times: 7.6 min for $^{18}$F-TFB, 7.8 min for $^{18}$F-TFB). Chemical purity and specific activity were analyzed by anion chromatography HPLC (retention times: 3.5 min for fluoride, 4.3 min for chloride, and 7.6 min for $BF_4^-$). Residual organic solvents were analyzed by GC (helium carrier gas flow at 10 cc/min through a MXTWAX column (Restek, Bellefonte, Pa., 0.53 mm ID, 30 m length)).

In Vivo Imaging

Studies with mice were performed under approval of the Mayo Clinic Institutional Animal Care and Use Committee. Dynamic PET imaging was performed in hNIS-expressing C6 glioma xenografted athymic mice following retro-orbital injection ~1.1 MBq Na $^{18}$F-TFB at different specific activities (10-0.001 mg TFB/Kg mouse) to assess hNIS activity with $^{18}$F-TFB. In this xenograft model, one flank has hNIS-negative C6 glioma tumor xenograft and the other flank had hNIS-expressing C6 glioma xenograft.

PET scans were acquired for 60 min followed by an X-ray scan using the GENISYS4 PET imaging system (Sofie Biosciences, CA). The images from 40 hNIS-expressing C6 glioma xenografted mice were analyzed for Standardized Uptake Value (SUV) in tumor, stomach, and thyroid using AMIDE image processing software (20). The SUV in tumor was normalized with SUV in stomach to account for difference in $^{18}$F-TFB bioavailability in different animals due to competing uptake in normal organs like thyroid, salivary glands and stomach.

Immunohistochemistry

Tumors from 5 age-matched hNIS-expressing C6 glioma xenografted mice were harvested and formalin-fixed. The tumors were then equilibrated in 15% and 30% sucrose with phosphate buffer for 4 days, and frozen for cryo-sectioning. A series of adjacent sections were cut on a cryostat. Each section was 10 μm thick, and mounted onto charged slides (Superfrost Plus slides, Fisherbrand). After drying, the sections were blocked with 10% goat serum for 4 h at room temperature, followed by overnight incubation with 1:4000 dilution of rabbit Anti-human NIS antibody SJ1 (Imanis Life Sciences, Rochester, Minn.) in PBS with 10% goat serum at 4° C. The non-specific anti-human NIS antibody SJ1 in sections was 3× washed in PBS-Tween 20 (0.05%) for 15 min each at room temperature. The sections were incubated with secondary antibody, Alexa Fluor 488 goat anti-rabbit IgG (H+L) antibody (Life Technologies, CA) at a dilution of 1:4000 in PBS for 45 min at room temperature. The non-specific secondary antibody was thrice washed in PBS-Tween 20 (0.05%) for 15 min each at room temperature. Following washing, the sections were counter-stained with nuclear DAPI stain. The sections were then cover-slipped with mounting medium and imaged using a Nikon Eclipse Ti inverted microscope at 10× magnification.

Data Analysis and Statistics

Data is expressed as mean±SD. MicroSoft Excel Solver was used to regress the tumor/stomach ratios of $^{18}$F-TFB uptake using a nonlinear least-squares regression algorithm.

Results

Radiosynthesis and Quality Control of $^{18}$F-TFB

After irradiation, $^{18}$F-fluoride in $^{18}$O-enriched water was delivered to the hot cell and quantitatively trapped on the QMA cartridge. The QMA cartridge was rinsed with acetone (10 mL) and flushed with nitrogen for 100 s. The freshly prepared BF$_3$.THF complex solution (5 mL) was passed through an inhouse-made Lewatit® MP-64 cartridge and the QMA cartridge as a single bulk passage of solvent lasting ~10 s. $^{18}$F-TFB largely remained on the cartridge while 20-40% of the $^{18}$F-fluoride was released from the QMA cartridge, possibly by formation of $^{18}$F-HF under the acidic conditions caused by BF$_3$. The QMA cartridge was rinsed with a solution of 10 mL THE and 13 mL water to remove the impurities from the QMA cartridge. To decrease the residual acetone and THF in the final product, 100 s of nitrogen flush was applied after THF rinsing. $^{18}$F-TFB was eluted from the QMA cartridge with 5 mL sterile saline to the product vial, in which 5 mL sterile saline was added in advance for further dilution of the product. The crude product solution was purified by trapping the unreacted $^{18}$F-fluoride on three alumina-N SepPak Light cartridges. Using two alumina-N SepPak Light cartridges, the radio-chemical purities were 93-96%. Radiochemical purity was increased to >98% by use of an additional alumina-N SepPak Light cartridge. The amount of starting BF$_3$ for the reaction was found to be critical to determine the radio-chemical yields and specific activities. Firstly, 5 mL BF$_3$.THF/PE solution (~45 μmol) was used in the reaction and 8.33-0.65 μmol unlabeled TFB with 35.0±3.6% yields were obtained. To decrease the amount of BF$_3$ for the reaction, the BF$_3$.THF/PE solution was passed through Lewatit® MP-64 resin immediately before passage through the QMA cartridge. Lewatit® MP-64 is an anion exchange resin, which contains crosslinked polystyrene matrix with tertiary amine and quaternary ammonium functional groups. Separate analysis of the post-Lewatit® MP-64 filtrate showed that 70%, 80% and 90% of the BF$_3$ in the original 5 mL BF$_3$.THF/PE solution was retained on 200, 300 and 400 mg Lewatit® MP-64 resin, respectively. Thus, the influence of the Lewatit® MP-64 was not only to retain unlabeled TFB, but also to reduce the amount of BF$_3$ reactant. Evidently, the BF$_3$ tertiary amine complex formed on the Lewatit® MP-64 was stronger than the BF$_3$.THF complex in the solution, which result in retention of BF on the resin.

Figure 4:
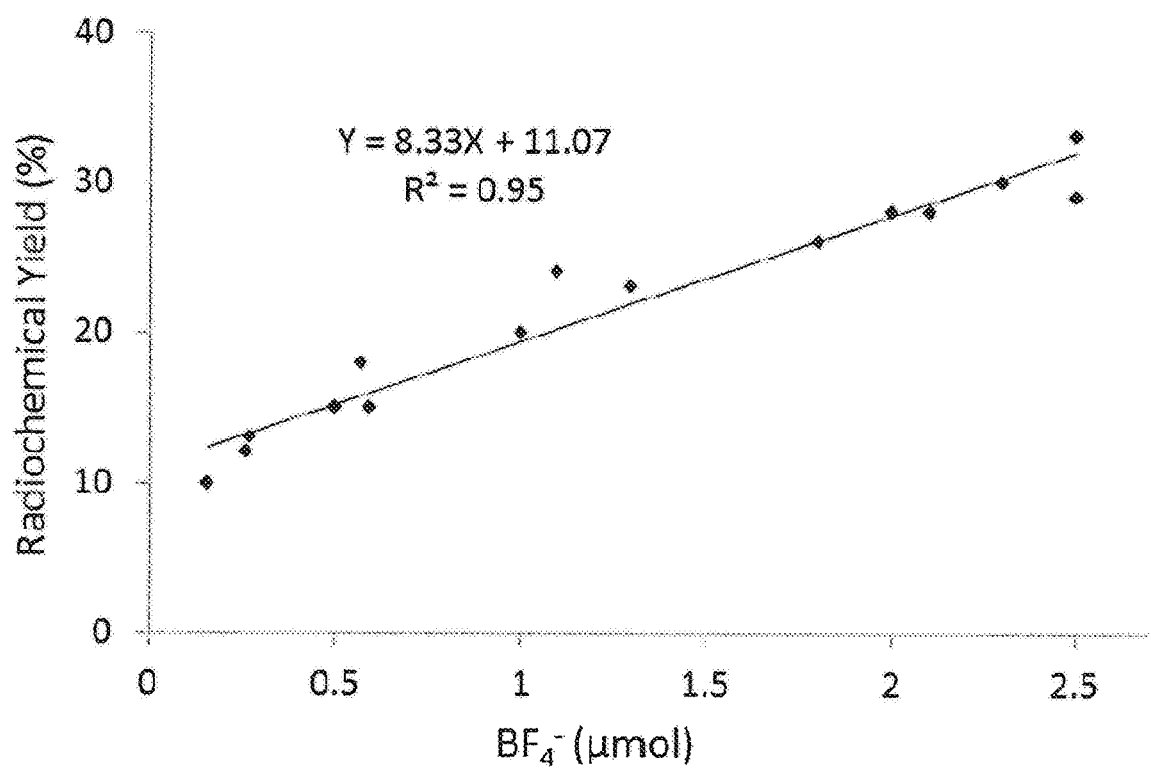
FIG. 4 depicts the relationship of radiochemical yields (uncorrected) to the amount of unlabeled $BF_4^-$ produced as found using different amounts of MP-64 resin to pre-filter the $BF_3$.THF/PE reagent (data from Table 1).

Investigations with 200 to 400 mg Lewatit® MP-64 resin (Table 1) resulted in the production of unlabeled TFB and product $^{18}$F-TFB in proportional amounts (FIG. 4). More Lewatit® MP-64 resin gave less BF$_3$ in the reaction, resulting in lower radiochemical yield with proportionately less unlabeled TFB (Table 1). Thus, the specific activity of the $^{18}$F-TFB product improved as the amount of Lewatit® MP-64 resin is increased, however, at the cost of decreased radiochemical yield.

TABLE 1

Dependence of overall radiochemical yield and specific activity (N = 3) of $^{18}$F-TFB product on the amount of Lewatit ™ MP-64 resin. Reactions were performed with starting $^{18}$F-fluoride radioactivities of 15-37 MBq.

| Lewatit ™ MP-64 resin (mg) | Unlabeled BF$_4^-$ (μmol) | Uncorrected radiochemical yield (%) |
|---|---|---|
| 0 | 8.33 ± 0.65 | 35.0 ± 3.6 |
| 200 | 2.43 ± 0.12 | 30.7 ± 2.1 |
| 250 | 1.97 ± 0.15 | 27.3 ± 1.2 |
| 300 | 1.13 ± 0.15 | 22.3 ± 2.1 |
| 350 | 0.55 ± 0.05 | 16.0 ± 1.7 |
| 400 | 0.23 ± 0.06 | 11.7 ± 1.5 |

Figure 5:
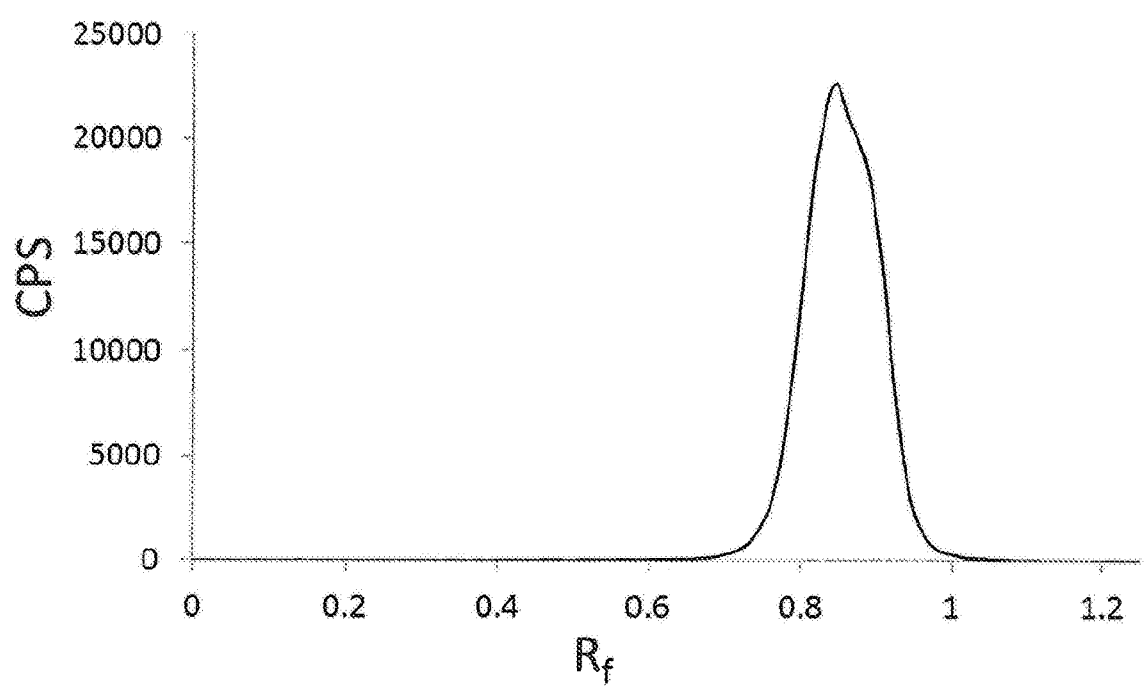
FIG. 5 is a graph showing radio-TLC of purified $^{18}$F-TFB (Rf=0.8-0.85) with the silica gel stationary phase and methanol mobile phase. If present, unreacted $^{18}$F-fluoride would remain at the origin.
Figure 6:
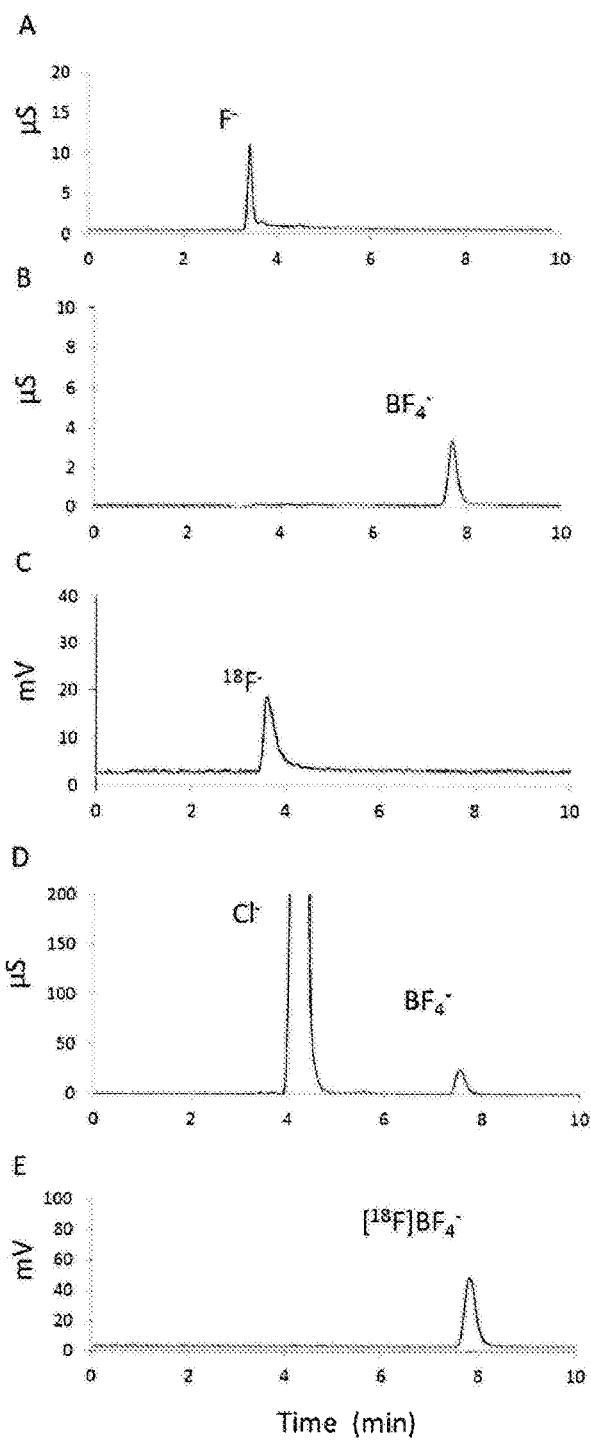
FIG. 6A depicts HPLC analysis of the $^{18}$F-TFB product in saline, conductivity data for 10 μg/mL NaF standard.
FIG. 6B depicts HPLC analysis of the $^{18}$F-TFB product in saline, conductivity data for 10 μg/mL NaBF4 standard.
FIG. 6C depicts HPLC analysis of the $^{18}$F-TFB product in saline, radioactivity data for 1.1 MBq $^{18}$F-fluoride standard.
FIG. 6D depicts HPLC analysis of the $^{18}$F-TFB product in saline, conductivity data for purified $^{18}$F-TFB in saline.
FIG. 6E depicts HPLC analysis of the $^{18}$F-TFB product in saline, radioactivity data for purified $^{18}$F-TFB in saline.

A 300 mg Lewatit® MP-64 resin was used for a high radioactivity level synthesis (40-44 GBq) as a compromise between radiochemical yield and specific activity. The radio-chemical yield of $^{18}$F-TFB was 20.0±0.7% (n=3) uncor-rected in a synthesis time of 10 min. Radiochemical purity was >98% as shown on silica gel TLC (FIG. 5) and anion chromatography HPLC (FIG. 6). Specific activities of 8.84±0.56 GBq/μmol (n=3) were achieved from starting $^{18}$F-fluoride activities of 40-44 GBq. In the HPLC analysis of the final product, a carbonate peak at 3.6 min and an unknown impurity peak at 3.8 min were initially observed. Investigation revealed these to be contaminants present on the stock QMA and alumina cartridges. By pretreating the cartridges with 20 mL 0.9% saline and 20 mL water, the peaks were reduced to a trace amount.

Figure 7:
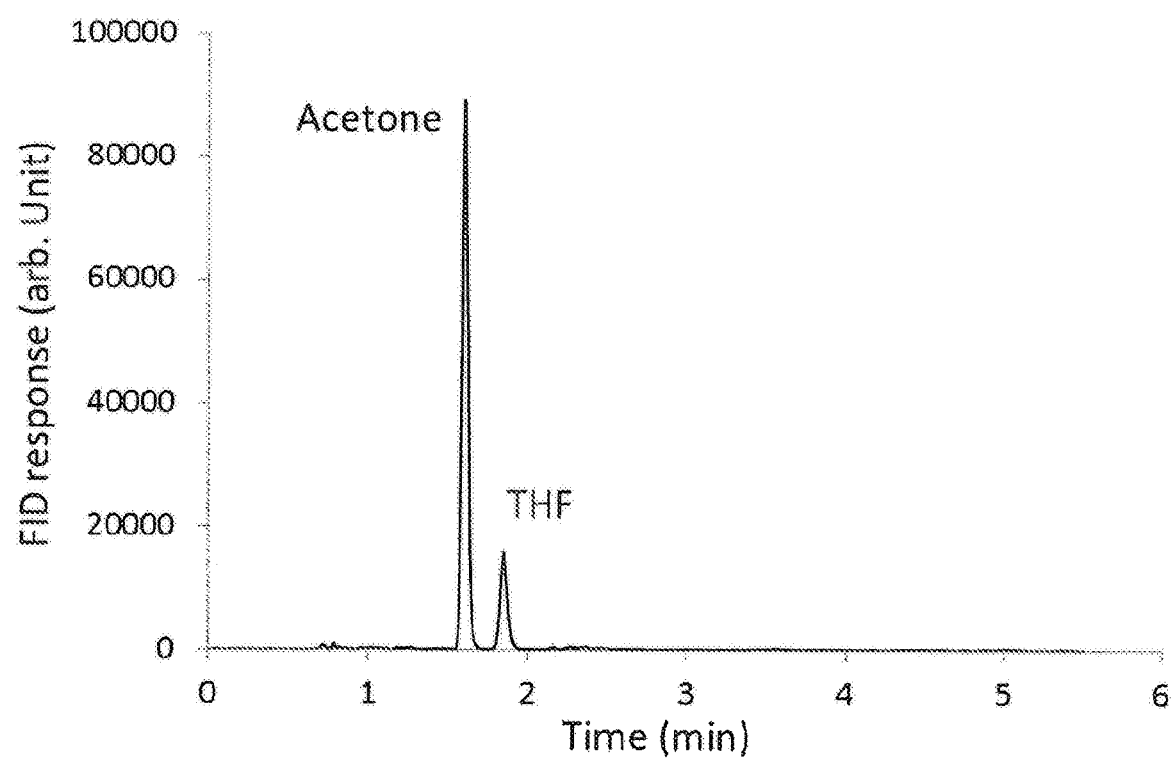
FIG. 7 shows GC analysis of residual organic solvents in the final $^{18}$F-TFB product. No obvious petroleum ether peaks were observed.
Figure 8:
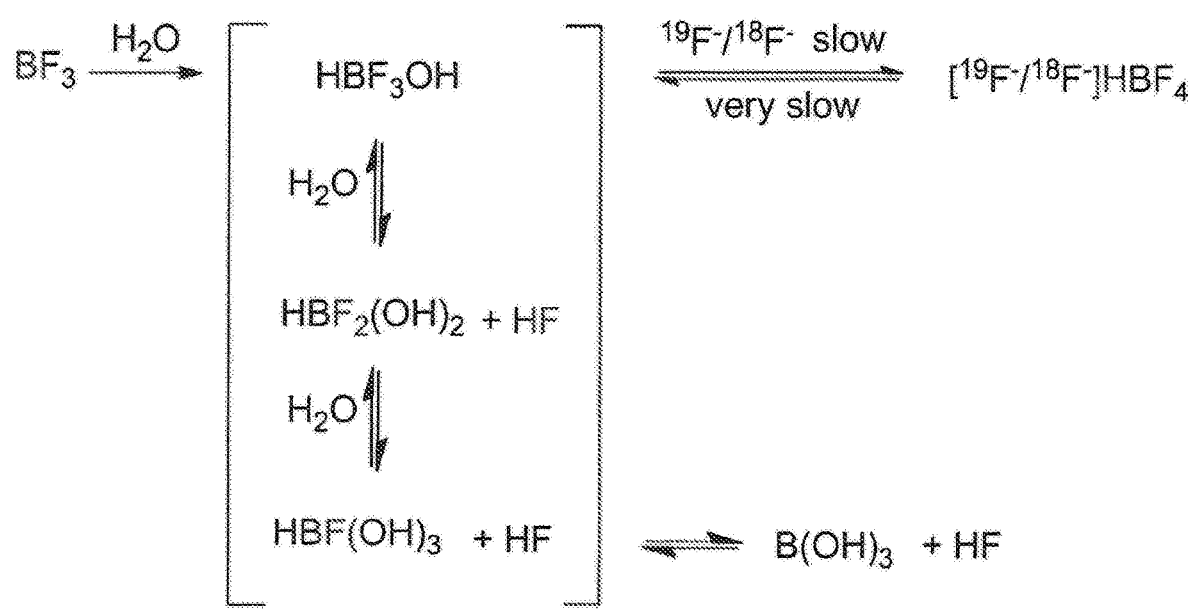
FIG. 8 is a schematic of the putative reaction scheme for formation of $^{19}$F/$^{18}$F-TFB from $BF_3$ of the preparation of $BF_3$.THF/PE complex solution.

Residual acetone and THF were obtained in concentrations of 63-135 ppm and 24-27 ppm, respectively, which were well under the allowed solvent concentration limits (acetone 5000 ppm, THF 720 ppm) set by the International Conference on Harmonization (ICH) for technical requirements for registration of pharmaceuticals for human use (FIG. 7).

Stability of $^{18}$F-TFB

After the synthesis, a sample was diluted with water for the analysis. With the eluent of methanol on silica gel plate, purities of >98% were obtained on the radio-TLC scanner. After 20 h, radio-TLC gave a >96% radiochemical purity and HPLC analysis of the product sample showed the $^{18}$F-TFB peak was chemically stable. A slow hydration of $^{18}$F-TFB in water may resulted in the slow decrement of the radiochemical purity. HPLC analysis of a NaBF$_4$ stock solution (stored for 7 month at room temperature) showed 50% of TFB was decayed and gave a peak of fluoride at 3.4 min.

In Vivo Imaging Studies

Figure 9A:
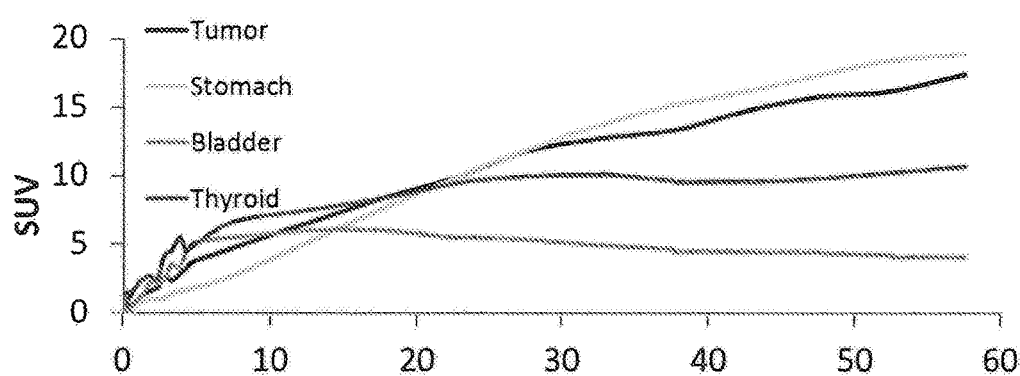
FIG. 9A is a graph depicting time dependence of $^{18}$F-TFB uptake (SUV) in different organs in representative hNIS-expressing C6 glioma xenografted mice at high specific activity of $^{18}$F-TFB (13 MBq/μmol or 0.37 mg/kg mouse weight).
Figure 9B:
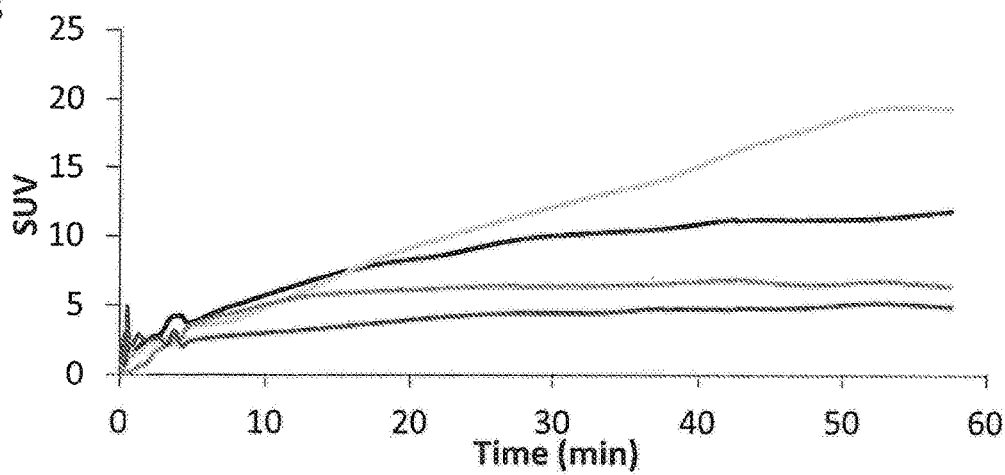
FIG. 9B is a graph depicting time dependence of $^{18}$F-TFB uptake (SUV) in different organs in representative hNIS-expressing C6 glioma xenografted mice at low specific activity of $^{18}$F-TFB (3 MBq/μmol or 1.6 mg/kg mouse weight).
Figure 10:
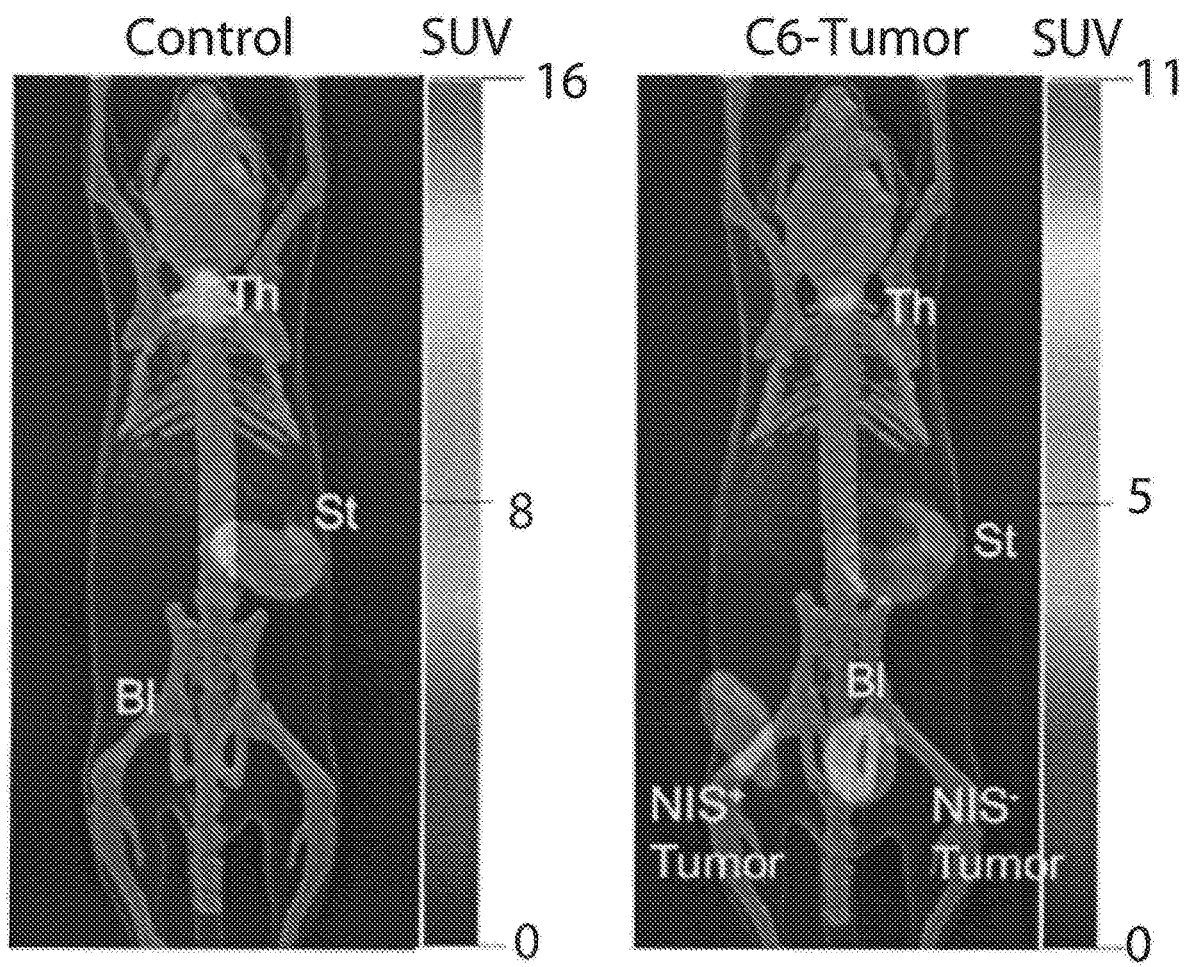
FIG. 10 depicts PET images of $^{18}$F-TFB distribution in control mouse (left) and a mouse bearing hNIS-positive and hNIS-negative C6 glioma xenografts (right). The overlaid reference bone atlas is computer generated.

Robust uptake of $^{18}$F-TFB was observed in thyroid, stomach, bladder and hNIS-expressing tumors of the C6-glioma xenograft mouse model (FIGS. 9 and 10), No uptake of $^{18}$F-TFB was observed in hNIS-negative tumors, confirming specificity of uptake of $^{18}$F-TFB to hNIS-expressing tumors. $^{18}$F-TFB uptake in thyroid and hNIS-expressing tumor showed a bi-phasic kinetic: rapid uptake over the first 10 min was followed by slower uptake until 30 min with little subsequent change. The stomach showed linear increase in $^{18}$F-TFB uptake over 60 min. Stomach uptake was independent of specific activity of $^{18}$F-TFB while uptake in hNIS-expressing tumor and thyroid was dependent on specific activity of $^{18}$F-TFB. The uptake of $^{18}$F-TFB by hNIS-expressing tumor was higher at high specific activity (>13 MBq/μmol) as compared to lower specific activity (3 MBq/μmol). This trend was also seen for thyroid.

Figure 11A:
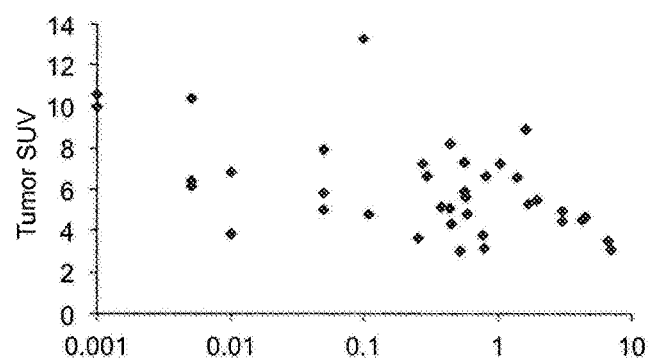
FIG. 11A depicts dependence of tumor of $^{18}$F-TFB uptake on administered mass of TFB to hNIS-expressing C6 glioma xenografted mice.
Figure 11B:
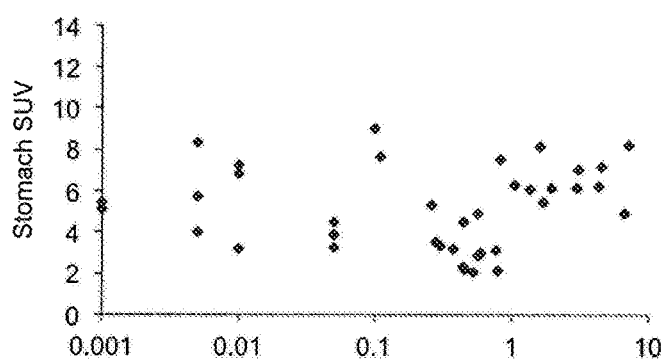
FIG. 11B depicts dependence of stomach of $^{18}$F-TFB uptake on administered mass of TFB to hNIS-expressing C6 glioma xenografted mice.
Figure 11C:
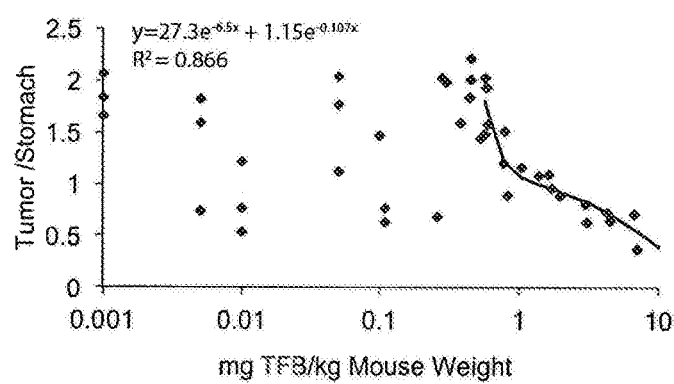
FIG. 11C depicts dependence of tumor/stomach ratio of $^{18}$F-TFB uptake on administered mass of TFB to hNIS-expressing C6 glioma xenografted mice. The tumor/stomach ratio data for administered mass >0.5 mg/kg was fit to a bi-exponential clearance model using non-linear least-squares regression. Microsoft Excel Solver was used to regress the tumor/stomach ratios using a nonlinear least-squares regression algorithm.
Figure 12:
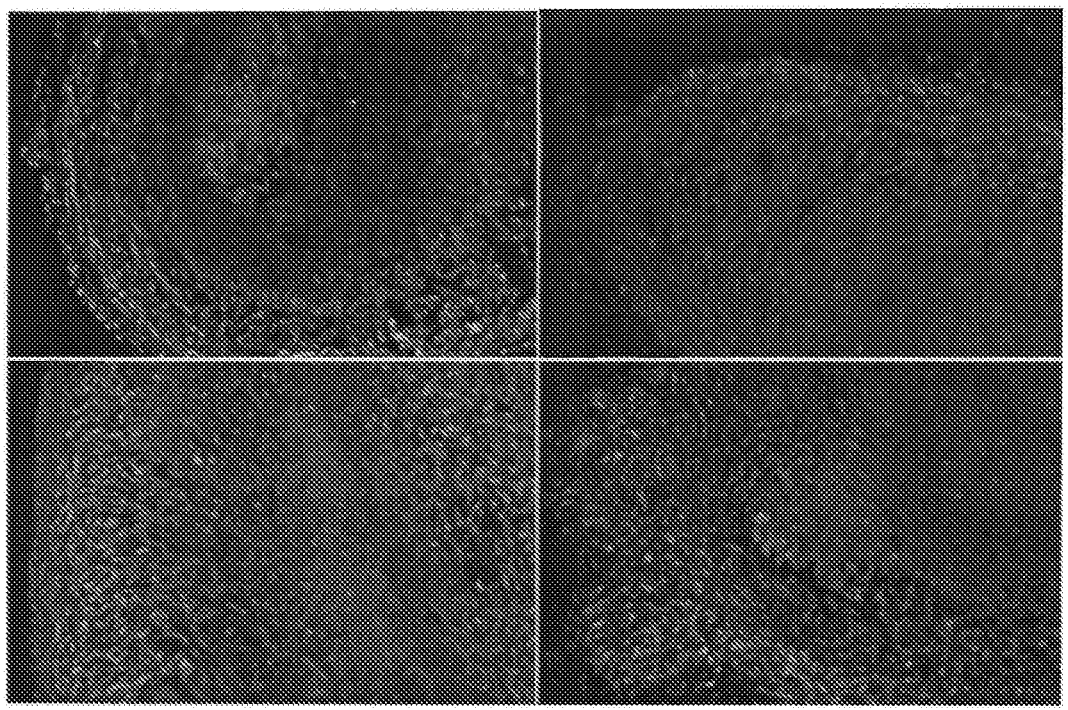
FIG. 12 are pictures representing immunostaining of hNIS-expressing C6 glioma xenografts (10× magnification) showing intra-tumoral and inter-tumoral variability of expression of hNIS. (Green: Alexa Fluor 488 antibody bound hNIS and Blue: DAPI stained nuclei)

For a more detailed analysis of the effect of specific activity of $^{18}$F-TFB on uptake in hNIS-expressing tumors, a 60 min time-point was chosen and a range of specific activities (10-0.001 mg TFB injected/kg mouse weight) was tested. The uptake in tumor was normalized to stomach uptake to account for differences in bioavailability of $^{18}$F-TFB across animals. The uptake of $^{18}$F-TFB in hNIS-expressing C6 tumor showed dependence on specific activity at 10-0.5 mg TFB/Kg mouse weight or 0-10 MBq/μmol considering ~1.1 MBq radioactivity injected in a ~25 g mice. But this trend was not observed for higher specific activities (>10 MB/μmol TFB or <0.5 mg TFB/Kg mouse weight) (FIG. 11). At these higher specific activities the uptake of $^{18}$F-TFB was no longer dependent on specific activity but exhibited high variability. Immunohistochemistry analysis for hNIS in tumor sections from 5 mice showed significant intra-tumoral and inter-tumoral variability of expression of hNIS (FIG. 12) that may play a role in the variability of $^{18}$F-TFB uptake observed in tumors.

Discussion

BF$_3$ is a versatile Lewis acid and widely used in the chemistry. It is known that BF$_3$ will form TFB in the presence of water via a fluoride exchange reaction, which was well documented [17, 18]. Therefore, the present disclosure aimed to synthesize high specific activity $^{18}$F-TFB with the reaction of BF$_3$ and $^{18}$F-fluoride. The $^{18}$F-fluoride was conveniently trapped on a QMA cartridge and the reaction was found to proceed by addition of a BF$_3$ complex in solution. A variety of BF$_3$ complexes (e.g. BF$_3$-pyridine, BF$_3$-Et$_3$N, BF$_3$-MeOH, BF$_3$-EtOH, BF$_3$.Et$_2$O and BF$_3$.THF) were tested in the reaction. With respect to yield and specific activity, BF$_3$.THF complex gave the best results. Therefore, BF$_3$.THF complex was used for the further optimization. In initial exploration, only 5-10% radiochemical yields of $^{18}$F-TFB were obtained with commercially available BF$_3$.THF solutions. To improve radiochemical yields of $^{18}$F-TFB, a BF$_3$.THF/PE solution was freshly prepared with BF$_3$ gas in a simple apparatus described above (FIG. 1A or 1B). To improve specific activity, the freshly prepared BF$_3$.THF/PE solution was passed through Lewatit® MP-64 resin immediately before passage through the QMA cartridge. As shown in Table 1, depending on the amount of Lewatit® MP-64 resin used in the process, a trade-off was found to exist between radiochemical yield and specific activity of the $^{18}$F-TFB product.

Using 300 mg Lewatit® MP-64 resin was selected for a high radioactivity level synthesis (40-44 GBq) as a compromise between radiochemical yield and specific activity. Three runs in this condition achieved specific activities of 8.84±0.56 GBq/.mol and uncorrected radiochemical yields of 20.0±0.7%. In some embodiments, to optimize specific activity at the sacrifice of radiochemical yield, the use of 400 mg Lewatit® MP-64 resin and 80 GBq starting activity would result in $^{18}$F-TFB specific activity of approximately 30 GBq/μmol with an overall uncorrected radiochemical yield near about 12%. The high specific activities obtained by our method are unlikely to be obtained with the previously reported isotope exchange method [14].

The methods provided improve upon the isotope exchange method by providing significantly enhanced radiochemical yields (~31% with use of 200 mg Lewatit® MP-64 resin versus ~10% for isotopic exchange [14]) at moderate specific activity (~5 GBq/μmol (estimated) versus ~1 GBq/μmol [14]). A putative chemical reaction mechanism for synthesis of $^{18}$F-TFB via BF$_3$ is shown in scheme 1. BF$_3$ hydrates with water quickly to form HBF$_3$OH [17]. Although the BF$_3$.THF complex solution is prepared in near anhydrous conditions, the QMA cartridge is likely containing trace amounts of water after trapping of the $^{18}$F-fluoride and treatment with acetone and nitrogen. Indeed, the $^{18}$F-fluoride itself may be in a hydrated form [19] on the QMA cartridge. Although it is possible that BF$_3$ reacts directly with $^{18}$F-fluoride ion, not to be bound by any theory, it is believed that HBF$_3$OH is the more likely intermediate to react with $^{18}$F-fluoride to make $^{18}$F-TFB. In the presence of water, HBF$_3$OH may react further to form a series of intermediates, which ends with the release of boric acid and HF [17]. The release of $^{19}$-fluoride from BF$_3$ may represent a source of unlabeled fluoride that can decrease the specific activity of the product. (Scheme 1)

Jauregui-Osoro et al. (14) estimated that the administration of ~400 MBq $^{18}$F-TFB synthesized by the conventional method to a human subject would result in a plasma concentration of ~0.1 μM TFB. Considering the IC$_{50}$ of TFB to be 0.1-1 μM for inhibition of iodine uptake by NIS in thyroid (21), it is desirable to increase $^{18}$F-TFB specific activity above ~5 GBq/μmol to avoid a pharmacological effect (14). The presently reported synthesis method for $^{18}$F-TFB achieves this goal. At a specific activity of 8 GBq/μmol, a ~400 MBq administered dose of $^{18}$F-TFB would give an estimated in vivo concentration of ~0.02 μM TFB which should not exhibit a pharmacologic effect.

To evaluate the influence of $^{18}$F-TFB specific activity on in vivo uptake by NIS-expressing tissues, we employed a hNIS-expressing C6 tumor xenograft mouse model. As expected, $^{18}$F-TFB was taken up by selected organs expressing NIS in the xenograft mouse model. Among the select organs, thyroid and hNIS-expressing tumor were sensitive to specific activity of $^{18}$F-TFB as $^{18}$F-TFB was being transported using NIS in these organs. On the other hand, in stomach, which also possesses NIS (22-24), the uptake of $^{18}$F-TFB was found to be independent of its specific activity. The insensitivity of $^{18}$F-TFB uptake to specific activity in stomach was not clarified, but may point to different kinetic properties of the NIS protein in gastric mucosal cells as compared to thyroid and hNIS-expressing tumor (23,24). Another possible explanation is that $^{18}$F-TFB entering the gastric epithelial cells is immediately effluxed into the stomach lumen such that the intracellular concentration (e.g. in gastric parietal cells) is never in equilibrium with the interstitial fluid so unidirectional transport continues unabated. A biphasic response was observed in hNIS-expressing tumor uptake of $^{18}$F-TFB versus administered dose of unlabeled TFB. The $^{18}$F-TFB uptake in tumor decreased with increasing amount of administered TFB over the range of 0.5-10 mg TFB/kg mouse weight, but this trend was not observed for higher specific activities (<0.5 mg TFB/kg mouse weight). Rather, the tumor uptake was constant but highly variable for administered TFB doses <0.5 mg/kg. The reason for this trend is not clear but it is possible that at high specific activity, factors other than specific activity contribute to the variability, such as variability in the inter- and intra-tumoral expression and/or activity of hNIS, number of tumor cells expressing hNIS, heterogeneity of tumor perfusion and/or oxygenation, variability of tumor size or the indirect influence of differences in the physiological distribution of radiotracer to other areas of the body. The large variation seen in hNIS expression levels in the C6 glioma xenografts may reflect the fact that the C6-hNIS transduced cell line was not a clonal population but included high, low and negative expressing cells. The ability of the $^{18}$F-TFB-PET method to reliably report on viral infection depends on hNIS expression within infected cells and possibly post-translational events that influence hNIS transporter activity (25). These considerations must also be kept in mind for future studies in monitoring hNIS transduction in human studies that may also entail significant heterogeneity of hNIS expression following viral therapies. Nonetheless, it was encouraging to observe a broad range of specific activities of $^{18}$F-TFB over which tumor uptake was robust.

Conclusion

A solid-phase supported synthesis of $^{18}$F-TFB was developed via radiofluorination of BF$_3$. With the optimized condition, the radiochemical yield of $^{18}$F-TFB was 20.0±0.7% (n=3) uncorrected in a synthesis time of 10 min. Specific activities of 8.84±0.56 GBq/μmol (n=3) were achieved with starting $^{18}$F-fluoride radioativities of 40-44 GBq. This method offers a convenient synthesis of high specific activity $^{18}$F-TFB. A positive correlation was observed between specific activity of $^{18}$F-TFB and hNIS-expressing C6 glioma xenografts for lower specific activities resulting in administration of TFB exceeding 0.5 mg/kg in mice. The increased specific activity of $^{18}$F-TFB may allow for enhanced PET imaging of hNIS reporter in future human studies.

REFERENCES FOR EXAMPLE 1

[1] Chung J K. Sodium iodide symporter: its role in nuclear medicine. J Nucl Med 2002; 43:1188-200.
[2] Penheiter A R, Russell S J, and Carlson S K. The sodium iodide symporter (NIS) as an imaging reporter for gene, viral, and cell-based therapies. Curr Gene Ther 2012; 12:33-47.
[3] Ahn B-C. Sodium Iodide Symporter for nuclear molecular imaging and gene therapy: from bedside to bench and back. Theranostics 2012; 2:392-402.
[4] Daniels G H and Haber D A. Will radioiodine be useful in treatment of breast cancer? Nat Med 2000; 6:859-60.
[5] Dai G, Levy O, and Carrasco N. Cloning and characterization of the thyroid iodide transporter. Nature 1996; 379:458-60.
[6] Eskandari S, Loo D D F, Dai G, Levy O, Wright E M, and Carrasco N. Thyroid Na+/I. Symporter: mechanism, stoichiometry, and specificity. J. Biol. Chem 1997; 272: 27230-8.
[7] Sparagana M, Little A, and Kaplan E. Rapid evaluation of thyroid nodules using 99mTc-Pertechnetate scanning. J Nucl Med 1970; 11:224-5.
[8] Ryo U Y, Vaidya P V, Schneider A B, Bekerman C, and Pinsky S M. Thyroid imaging agents: a comparison of I-123 and Tc-99m pertechnetate. Radiology 1983; 148: 819-22.
[9] Groot-Wassink T, Aboagye E O, Wang Y, Lemoine N R, Reader A J, and Vassaux G. Quantitative imaging of Na/I Symporter transgene expression using positron emission tomography in the living animal. Mol Ther 2004; 9:436-42.
[10] Schmitz J. The production of [124I]iodine and [86Y] yttrium. Eur. J. Nucl. Med. Mol. Imag 2011; 38:4-9.
[11] Anbar M, Guttmann S, and Lewitus Z. The Accumulation of Fluoroborate Ions in Thyroid Glands of RatS1. Endocrinology 1960; 66:888-90.
[12] Anbar M, Guttmann S, and Lewitus Z. Effect of Monofluorosulphonate, Difluorophosphate and Fluoroborate Ions on the Iodine Uptake of the Thyroid Gland. Nature 1959; 183:1517-8.
[13] Anbar M and Guttmann S. The Isotopic Exchange of Fluoroboric Acid with Hydrofluoride Acid. J. Phys. Chem 1960; 64:1896-9.
[14] Jauregui-Osoro M, Sunassee K, Weeks A J, Berry D J, Paul R L, Cleij M, et al. Synthesis and biological evaluation of F-18 tetrafluoroborate: a PET imaging agent for thyroid disease and reporter gene imaging of the sodium/iodide symporter. Eur. J. Nucl. Med. Mol. Imag 2010; 37:2108-16.
[15] Weeks A J, Jauregui-Osoro M, Cleij M, Blower J E, Ballinger J R, and Blower P J. Evaluation of [$^{18}$F tetrafluoroborate as a potential PET imaging agent for the human sodium/iodide symporter in a new colon carcinoma cell line, HCT116, expressing hNIS. Nuclear Medicine Communications 2011; 32:98-105.
[16] Youn H, Jeong J M, and Chung J-K. A new PET probe, F-18-tetrafluoroborate, for the sodium/iodide symporter: possible impacts on nuclear medicine. Eur. J. Nucl. Med. Mol. Imag. 2010; 37:2105-7.
[17] Wamser C A. Equilibria in the System Boron Trifluoride-Water at 25<C. J. Am. Chem. Soc 1951; 73:409-16.
[18] Wamser C A. Hydrolysis of Fluoboric Acid in Aqueous Solution. J. Am. Chem. Soc 1948; 70:1209-15.
[19] Cai L, Lu S, and Pike V W. Chemistry with F-18 fluoride ion. Eur. J. Org. Chem 2008:2853 73.
[20]. Loening A M, Gambhir S S. AMIDE: a free software tool for multimodality medical image analysis. Mol Imaging. 2003; 2:131-137.
[21]. Lecat-Guillet N, Ambroise Y. Discovery of aryltrifluoroborates as potent sodium/iodide symporter (NIS) inhibitors. Chem Med Chem. 2008; 3:1207-1209.
[22]. Portulano C, Paroder-Belenitsky M, Carrasco N. The Na+/I− symporter (NIS): mechanism and medical impact. Endocr Rev. 2014; 35:106-149.
[23]. Wolosin J M. Ion transport studies with H+-K+-ATPase-rich vesicles: implications for HCl secretion and parietal cell physiology. Am J Physiol. 1985; 248:G595-607.
[24]. R. McG. Harden, W. D. Alexander, J. Shimmins, D. Chisholm. A comparison between the gastric and salivary concentration of iodide, pertechnetate, and bromide in man. Gut. 1969; 10:928-930.
[25]. Kogai T I, Brent G A. The sodium iodide symporter (NIS): regulation and approaches to targeting for cancer therapeutics. Pharmacol Ther. 2012; 135:35

The citation of any document is not to be construed as an admission that it is prior art with respect to the present invention.

Example 2: Biodistribution and Radiation Dosimetry of $^{18}$F-Tetrafluoroborate ($^{18}$F-TFB) in Healthy Human Subjects $^{18}$F-tetrafluoroborate ($^{18}$F-TFB) has been identified as a promising iodide analog for imaging of thyroid cancer and monitoring of NIS expression as a reporter probe in viral therapy applications. This Example demonstrates the pharmacokinetics, biodistribution and radiation dosimetry of high-specific activity $^{18}$F-TFB in healthy human subjects. Methods: $^{18}$F-TFB was synthesized via $^{18}$F-fluorination of BF$_3$ with specific activity of 2.2±0.9 GBq/µmol. Dynamic PET/CT imaging over 4 h was performed after intravenous administration of $^{18}$F-TFB (333-407 MBq) in 4 female and 4 male healthy volunteers (35±10 year old). Initial scanning over the heart allowed definition of the blood pharmacokinetics, while whole body scans at 2 and 3.5 h provided data for biodistribution and radiation dosimetry. Samples of venous blood and urine were collected over the imaging period and analyzed by ion-chromatography HPLC to determine tracer stability. Vital signs and clinical laboratory safety assays were measured to determine the safety of $^{18}$F-TFB administration. Results: $^{18}$F-TFB administration was well tolerated with no significant findings on vital signs or clinical laboratory assays. Left-ventricular blood pool time-activity curves showed a multi-phasic blood clearance of radioactivity with the two rapid clearance phases over the first 30-45 min, followed by a slower clearance phase. HPLC analysis showed insignificant $^{18}$F-labeled metabolites in the blood and urine over the length of the study (4 h). At 2 h p.i., high uptakes were seen in thyroid, stomach, salivary glands, and kidney. Urinary clearance of $^{18}$F-TFB was prominent. Minor changes were seen in $^{18}$F-TFB biodistribution from 2-4 h p.i. A low level of metabolic defluorination was evidenced by low accumulation of $^{18}$F-radioactivity in bone (SUV=1.4±0.5 in males, SUV=1.3±0.9 in females at 3.5 h). Conclusion: This initial study in healthy human subjects showed $^{18}$F-TFB to be safe, metabolically stable, and distribute in the human body similar to other iodide analogs with prominent physiologic distribution to thyroid, stomach, salivary glands and bladder, with thyroid as the dose-critical organ. $^{18}$F-TFB can be used as a hNIS gene reporter and imaging biomarker for thyroid cancer and other disease processes that import iodide.

Example 1 demonstrates high specific radioactivity syntheses of $^{18}$F-TFB via the reaction of boron trifluoride (BF$_3$) and $^{18}$F-fluoride. We demonstrated the relationship of $^{18}$F-TFB specific radioactivity and PET-delineated radiotracer uptake in NIS-transfected C6-glioma xenograft bearing mice, confirming the desirability of high specific radioactivity to avoid saturation effects at the NIS transporter. In this study, we report PET/CT imaging data with $^{18}$F-TFB in healthy male and female participants to describe physiologic distribution of the radiotracer and allow calculation of radiation dosimetry estimates.

Materials and Methods

Radiotracer Synthesis $^{18}$F-TFB was prepared and formulated in sterile 0.9% NaCl under cGMP conditions as previously described (12). Decay-corrected radiochemical yields of 32±2% and radiochemical purities (RCPs) >98% were obtained. Specific radioactivity of 2.2±0.9 GBq/µmol was achieved from starting $^{18}$F-fluoride radioactivity of 20-31 GBq. In vitro RCP remained >96% up to 8 h at room temperature.

Human Participants

Approval of the study was obtained from the Mayo Clinic Institutional Review Board and all participants provided informed consent. Four male (36±14 y) and four female (35±8 y) healthy volunteers were enrolled in the study. Participants were excluded that had previous diagnosis of cancer or clinically significant cardiovascular, renal, pulmonary, metabolic, and endocrine (thyroid) diseases. Participants were not required to fast prior to the imaging study but instructed to remain well-hydrated.

PET/CT Imaging Protocol

Figure 13:
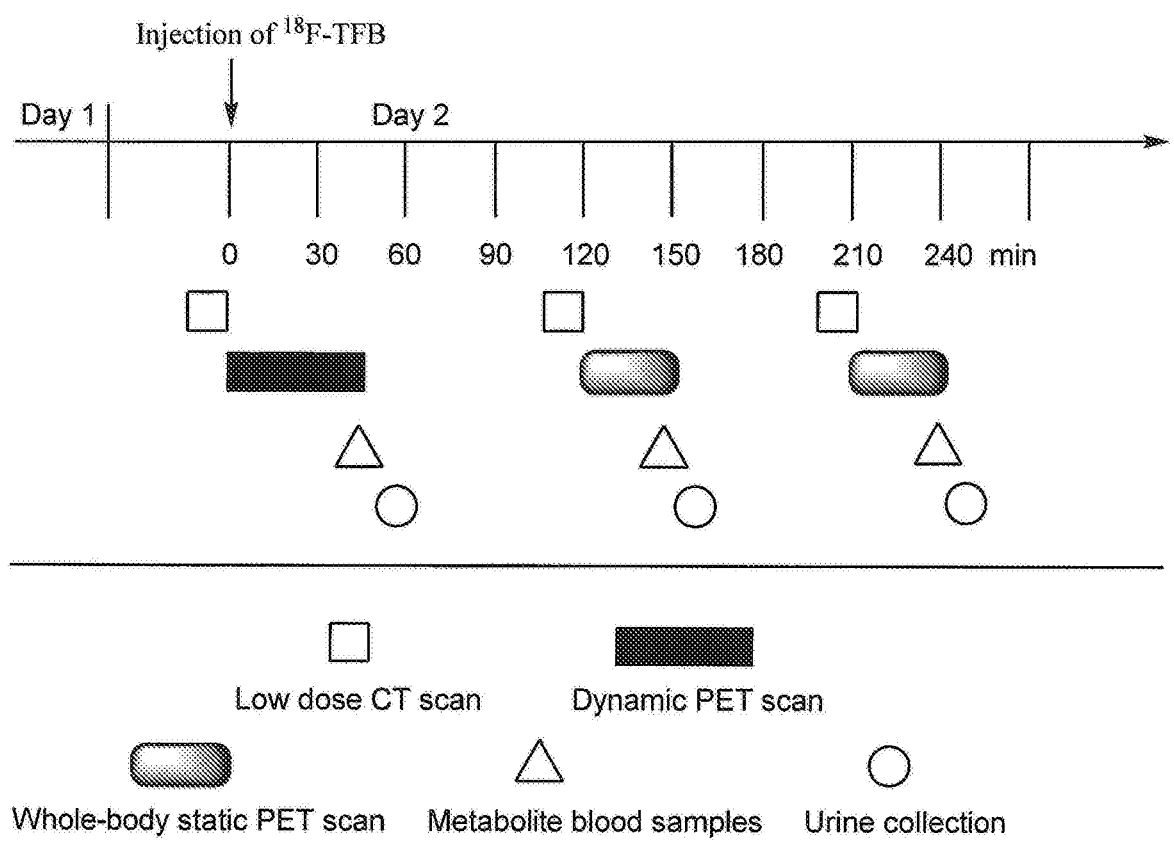
FIG. 13 is a schematic representation of the imaging protocol. Patients were screened on day 1 and imaged by $^{18}$F-TFB PET/CT on day 2.

The imaging protocol is illustrated in FIG. 13. After voiding of the bladder, participants were positioned in a GE 690XT PET/CT scanner (GE HealthCare, Waukesha, Wis.) in a supine position with the heart in the center of the axial field of view. Intravenous catheters were placed in both arms for radiotracer injection and blood sampling. Computed tomography scans of the thorax were initially acquired in the preparation for a dynamic PET data acquisition over the heart for the first 45 min following commencement of radiotracer administration. $^{18}$F-TFB (333-407 MBq) was administered over 1 minute into one of the catheters. The frame sequence for initial dynamic PET acquisition was 15×4, 8×15, 4×30, and 8×300 seconds. Following the dynamic heart scan, the participants were allowed a break from the scanner, during which time voided their bladders. Two additional PET/CT scans, from the vertex of the skull to mid-thigh, were performed at 2 hours and 3.5 hours respectively. The last PET/CT scan was completed ~4 h post-injection.

Measurements in Venous Blood and Urine Samples

Urine was collected after each PET/CT scan (approximately 55, 160, 250 min), and venous blood samples were collected at 40, 145 and 235 min, post-injection, as shown in FIG. 13. Blood samples (3-4 mL) were collected in heparinized tubes and placed on ice. The blood samples were centrifuged at 3000 g for 5 min to obtain plasma. Urine was measured for urine volume and radioactivity concentration as measured in a calibrated gamma counter. Analysis for metabolites in plasma and urine was performed by ion-chromatography HPLC, allowing estimation of the fraction of radioactivity as nonmetabolized $^{18}$F-TFB.

Safety Measurements for $^{18}$F-TFB Administration

Vital signs (heart rate, systolic and diastolic blood pressures, respiratory rate, and temperature) were measured prior to $^{18}$F-TFB administration and at 45 and 240 min post-injection. Venous blood samples were taken prior to $^{18}$F-TFB administration and at ~240 min post-injection for a panel of clinical laboratory tests to evaluate the safety of the radiotracer administration.

PET/CT Image Analysis

All PET scans images were reconstructed using 3D OSEM and time-of-flight reconstruction. Volumes of interest (VOI's) of organs were drawn using PMOD software (Ver. 3.5). Standardized Uptake Values (SUVs) normalized to body weight were then calculated for each VOI. Time-activity curves (TACs) were evaluated from the initial dynamic scan over the heart for left-ventricular blood pool, lung and liver regions.

Radiation Dosimetry Estimation

Radiation dosimetry estimates were calculated from organ residence times using OLINDA software (Ver. 1.1), assuming a bladder voiding interval of 3.5 h. Gender-specific organ masses for the conversion of SUV to disintegrations per organ per unit radioactivity administered (Bq-hr/Bq) were taken from Schlein et al. (15).

Statistics

Data are expressed as mean SD. Statistical significance of differences in SUV values between PET/CT scans were determined by ANOVA.

Results

Pharmacokinetics of $^{18}$F-TFB

Figure 14:
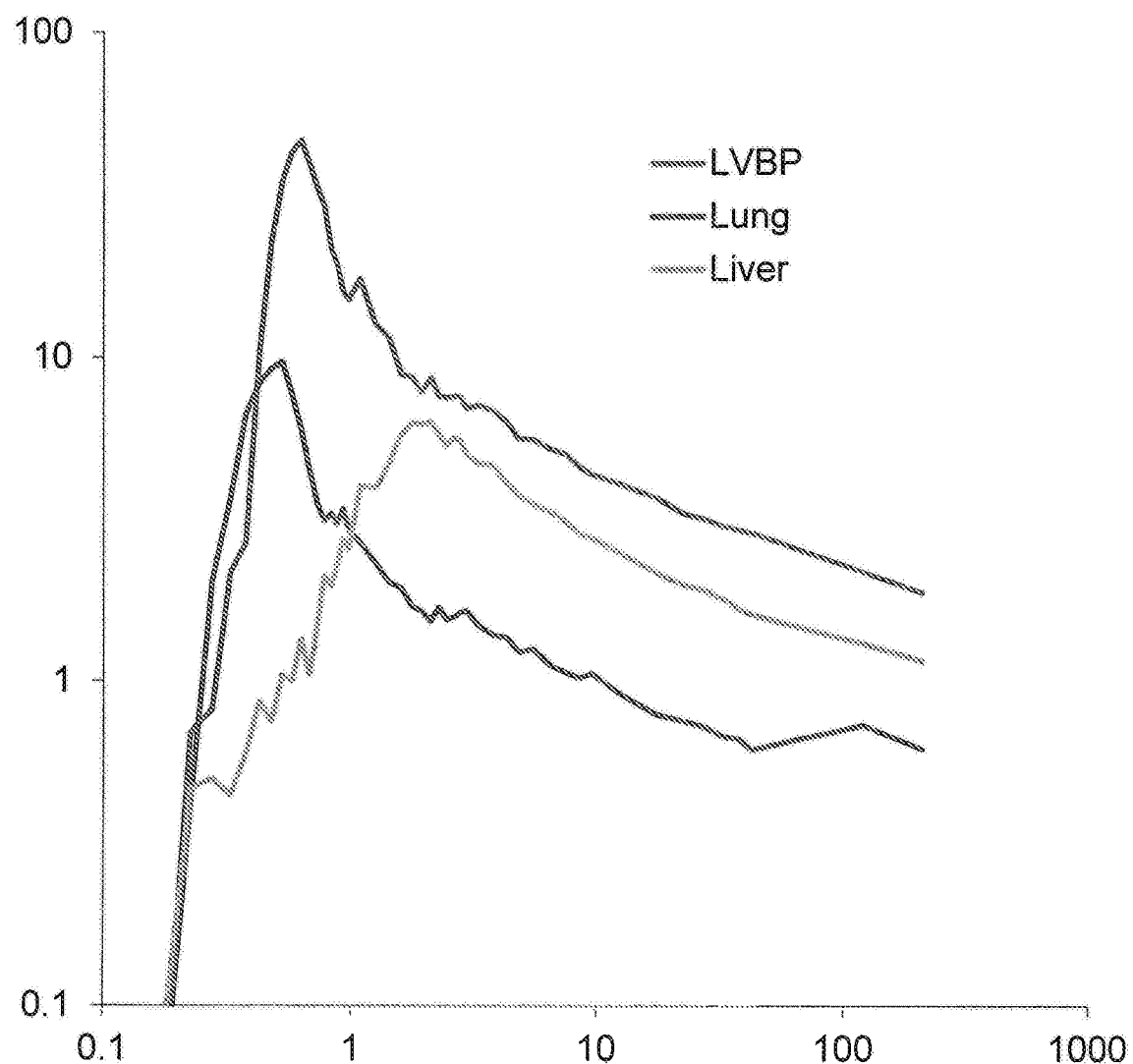
FIG. 14 depicts a graph showing time-activity curves of $^{18}$F-TFB in healthy mail participant. LVBP=left-ventricular blood pool.

The initial 45-min dynamic PET/CT scan over the heart allowed evaluation of the early kinetics of $^{18}$F-TFB in the left-ventricular blood pool (LVBP) as in indication of the pharmacokinetics of this radiotracer. FIG. 14 shows the time-activity curves in LVBP, lung, and liver in a representative participant. Peak values of radioactivity concentration were seen at ~1 min for LVBP and lung regions, whereas the peak in liver was at ~2 min post-administration of $^{18}$F-TFB. Blood clearance was multiphasic, with clearance proceeding to the end of the 4-h measurement period. Continued radiotracer washout was also seen in lung and liver.

Metabolite Analysis

HPLC metabolite analysis of plasma samples at 40 min p.i. showed >97% of radioactivity to be in the form of metabolically intact $^{18}$F-TFB (Table 2). Similarly, all urine samples taken from urine collections at approximately 50, 160, 250 min showed >97% of radioactivity in the form of $^{18}$F-TFB. The accumulated percentage of administered $^{18}$F-TFB in the urine at the end of study (~250 min) was 40±4% for males and 47±7% for females. Thus, renal clearance of nonmetabolized $^{18}$F-TFB is a major excretion pathway for $^{18}$F-TFB.

TABLE 2

Metabolite analysis of $^{18}$F-TFB in plasma and urine of healthy participants

|  | 40 min[a] | | 145 min[a] | | 235 min[a] | | Accumulative | |
| --- | --- | --- | --- | --- | --- | --- | --- | --- |
|  | Males | Females | Males | Females | Males | Females | Males | Females |
| Whole blood (SUV) | 3.0 ± 0.2 | 3.1 ± 0.9 | 2.1 ± 0.2 | 1.7 ± 0.4 | 1.7 ± 0.2 | 1.4 ± 0.4 | — | — |
| Plasma (SUV) | 3.8 ± 0.2 | 3.8 ± 1.0 | 2.8 ± 0.3 | 2.1 ± 0.5 | 2.0 ± 0.1 | 1.7 ± 0.5 | — | — |
| Urine (% Dose) | 15 ± 2[b] | 16 ± 3 | 13 ± 3 | 18 ± 3 | 10 ± 2[b] | 12 ± 2 | 40 ± 4[b] | 47 ± 7 |
| % Intact Plasma | 97 ± 2 | 97 ± 3[c] | —[d] | —[d] | —[d] | —[d] | — | — |
| $^{18}$F-TFB Urine | 96 ± 2 | 98 ± 1 | 97 ± 2 | 98 ± 1 | 98 ± 1 | 97 ± 2 | — | — |

Values are mean ± SEM (n = 4)
[a]Time-points are shown for blood samples; urine samples were collected ~10 min later.
[b]No urine in third collection in one of the male subjects.
[c]One plasma sample was not used because precipitate was observed in the HPLC analysis.
[d]Metabolite data were not obtained in second and third plasma samples analysis because the low radioactivity levels were below detection limit.

Biodistribution of $^{18}$F-TFB

Figure 15A:
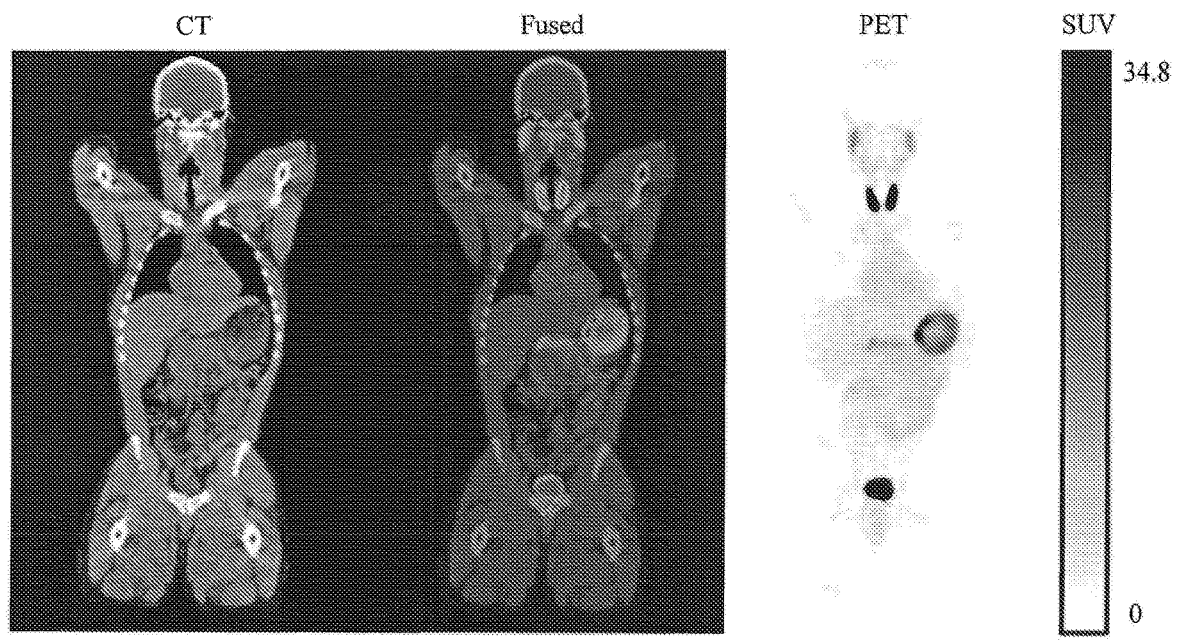
FIG. 15A are coronal PET/CT images of $^{18}$F-TFB in healthy male participants at 2 hour post-injection. Physiologic distribution of $^{18}$F-TFB is seen in thyroid, salivary glands, stomach and intestines. Prominent excretion of radioactivity is seen in urinary bladder.
Figure 15B:
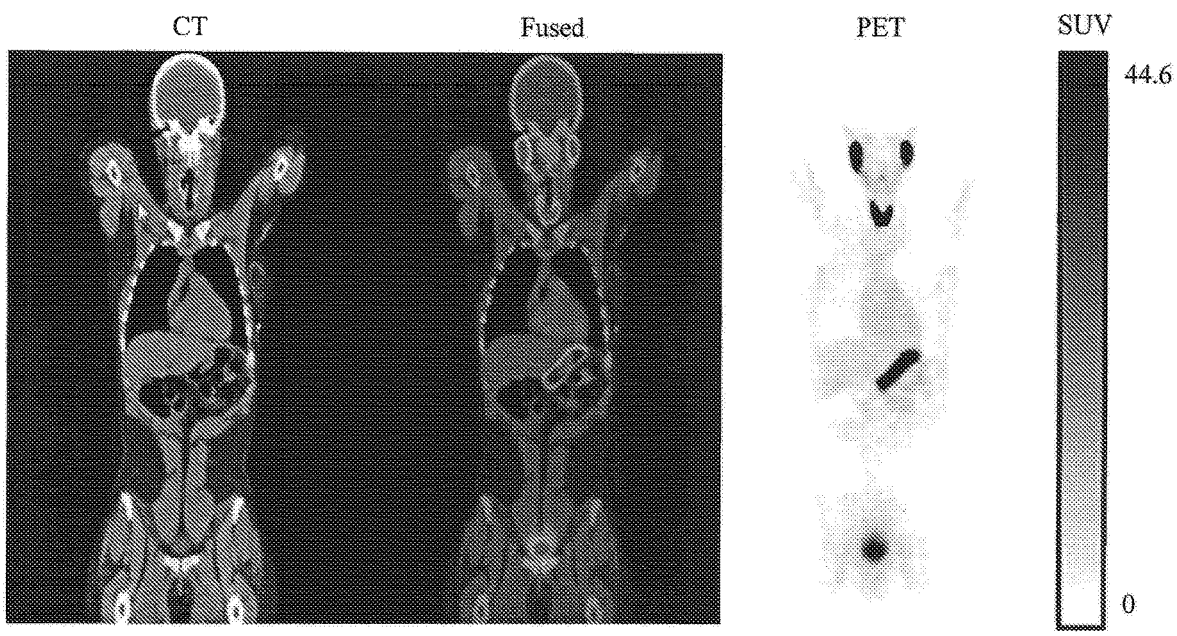
FIG. 15B are coronal PET/CT images of $^{18}$F-TFB in healthy female participants at 2 hour post-injection. Physiologic distribution of $^{18}$F-TFB is seen in thyroid, salivary glands, stomach and intestines. Prominent excretion of radioactivity is seen in urinary bladder.

Representative images from the whole-body PET/CT scan at 2 h post-injection are shown in FIG. 15 and the biodistribution data are summarized in Table 3. Robust uptake of $^{18}$F-TFB was observed in thyroid, stomach, salivary glands, and kidney. Prominent clearance of tracer through kidney to bladder was also observed. Minor differences were observed in the SUV values between the first (2 h) and second (3.5 h) whole body PET/CT scans, showing the tracer distribution to be stable at least after 2 h. Bone uptake was moderately increased from 2 to 3.5 h in males, indicating a low level of defluorination of $^{18}$F-TFB, but the increase was not statistically significant in females.

TABLE 3

PET/CT-derived distribution of $^{18}$F-TFB in healthy participants

|  | 2 h post-injection (SUV) | | 3.5 h post-injection (SUV) | |
| --- | --- | --- | --- | --- |
| Organ | Males | Females | Males | Females |
| Bone | 0.80 ± 0.33 | 0.74 ± 0.20 | 1.4 ± 0.5* | 1.3 ± 0.9 |
| Brain | 0.39 ± 0.14 | 0.42 ± 0.15 | 0.74 ± 0.26 | 0.61 ± 0.34 |
| Breast | — | 2.8 ± 0.4 | — | 3.9 ± 1.4 |
| Gallbladder | 2.7 ± 1.5 | 3.7 ± 1.0 | 4.2 ± 1.7 | 5.0 ± 1.6 |
| Intestines | 2.9 ± 1.0 | 5.0 ± 2.7 | 4.4 ± 1.0 | 6.0 ± 3.1 |
| Kidney | 7.0 ± 2.5 | 5.6 ± 0.7 | 11 ± 3 | 6.3 ± 2.4 |
| Liver | 2.3 ± 1.0 | 2.7 ± 0.5 | 3.6 ± 1.2 | 3.5 ± 1.6 |
| Lung | 1.0 ± 0.4 | 1.2 ± 0.4 | 1.7 ± 0.6 | 1.5 ± 0.8 |
| Muscle | 0.71 ± 0.31 | 0.65 ± 0.35 | 0.96 ± 0.31 | 0.78 ± 0.54 |
| Myocardium | 3.2 ± 0.9 | 2.8 ± 0.5 | 5.0 ± 0.9 | 3.8 ± 1.8 |
| Pancreas | 3.4 ± 0.7 | 3.1 ± 1.7 | 6.2 ± 2.1 | 3.0 ± 1.2 |
| Parotid | 11 ± 9 | 20 ± 11 | 16 ± 13 | 25 ± 15 |
| Spleen | 4.1 ± 1.2 | 4.3 ± 1.0 | 6.3 ± 1.1 | 5.5 ± 2.8 |
| Stomach | 33 ± 15 | 72 ± 10 | 70 ± 32 | 51 ± 18 |
| Thyroid | 55 ± 31 | 50 ± 11 | 82 ± 42* | 58 ± 12 |

Values are mean ± SEM (n = 4)
*p < 0.05 versus 2 h

Radiation Dosimetry Estimates

Table 4 shows organ residence times derived from the biodistribution data. Bladder residence time was estimated by the bladder emptying model within the OLINDA software, assuming a 3.5 h bladder voiding period. Estimated organ absorbed doses are shown in Table 5. The dose-critical organ is thyroid, with dose estimates of 0.26 and 0.36 mSv/MBq in males and females, respectively. The prominent excretion through the bladder resulted in moderately high doses to the bladder wall, with doses depending on voiding frequency. Effective doses are shown in Table 6. Effective dose was higher in females (0.065 mSv/MBq) relative to males (0.036 mSv/MBq).

TABLE 4

Organ residence times of $^{18}$F-TFB in healthy participants

| Organ | Residence Time Males (min) | Residence Time Females (min) |
| --- | --- | --- |
| Bone | 4.6 ± 1.3 | 3.1 ± 0.3 |
| Brain | 1.2 ± 0.4 | 1.3 ± 0.2 |
| Breast | — | 2.8 ± 0.9 |
| Gallbladder | 0.06 ± 0.03 | 0.09 ± 0.04 |
| Intestines | 5.7 ± 1.9 | 13 ± 7 |
| Kidney | 4.2 ± 1.2 | 3.9 ± 0.8 |
| Liver | 8.3 ± 3.9 | 10 ± 2 |
| Lung | 2.1 ± 0.7 | 2.4 ± 0.2 |
| Muscle | 36 ± 14 | 26 ± 8 |
| Myocardium | 2.1 ± 0.6 | 1.8 ± 0.3 |
| Pancreas | 0.7 ± 0.3 | 0.58 ± 0.08 |
| Parotid | 1.7 ± 1.1 | 3.3 ± 1.2 |

TABLE 4-continued

Organ residence times of $^{18}$F-TFB in healthy participants

| Organ | Residence Time Males (min) | Residence Time Females (min) |
|---|---|---|
| Spleen | 1.5 ± 0.4 | 1.6 ± 0.2 |
| Stomach | 11 ± 5 | 24 ± 12 |
| Thyroid | 2.0 ± 0.7 | 2.3 ± 0.9 |
| Bladder | 17 ± 2 | 19 ± 4 |

Values are mean ± SEM (n = 4)

TABLE 5

Estimated absorbed radiation dose for $^{18}$F-TFB (mSv/MBq)

| | Dose (mSv/MBq) | |
|---|---|---|
| Organ | Males | Females |
| Adrenals | 0.008 | 0.012 |
| Brain | 0.004 | 0.005 |
| Breasts | 0.002 | 0.028 |
| Gallbladder Wall | 0.012 | 0.022 |
| Lower Large Intestine Wall | 0.009 | 0.015 |
| Small Intestine Wall | 0.027 | 0.066 |
| Stomach Wall | 0.076 | 0.184 |
| Upper Large Intestine Wall | 0.045 | 0.109 |
| Heart Wall | 0.024 | 0.030 |
| Kidneys | 0.049 | 0.052 |
| Liver | 0.021 | 0.033 |
| Lungs | 0.009 | 0.014 |
| Muscle | 0.008 | 0.011 |
| Ovaries | — | 0.020 |
| Pancreas | 0.034 | 0.043 |
| Red Marrow | 0.005 | 0.008 |
| Osteogenic Cells | 0.008 | 0.009 |
| Skin | 0.003 | 0.004 |
| Spleen | 0.033 | 0.047 |
| Testes | 0.005 | — |
| Thymus | 0.004 | 0.005 |
| Thyroid | 0.26 | 0.36 |
| Urinary Bladder Wall | 0.14 | 0.22 |
| Uterus | — | 0.022 |
| Total Body | 0.008 | 0.011 |

TABLE 6

Effective dose for $^{18}$F-TFB in healthy participants

| | Males | Females |
|---|---|---|
| Effective Dose (mSv/MBq) | 0.036 | 0.065 |

$^{18}$F-TFB Safety data

Vital signs (heart rate, diastolic and systolic blood pressures, and respiratory rate) were monitored before $^{18}$F-TFB administration and throughout the PET/CT imaging period. No significant changes in the vital signs were found after $^{18}$F-TFB administration (data not shown). Likewise, a panel of clinical laboratory blood tests was measured to assess for effects of $^{18}$F-TFB administration on blood chemistries, including electrolytes, and liver and kidney functional tests (Supplemental data not shown). No significant changes were observed in the clinical laboratory test values for the samples acquired after $^{18}$F-TFB administration relative to baseline.

Discussion

This Example evaluated the pharmacokinetics, biodistribution and radiation dosimetry of high specific radioactivity $^{18}$F-TFB in eight healthy human participants. The tracer was well-tolerated and no adverse effects were noted. hNIS is known to be highly expressed in certain tissues (thyroid, breast, stomach and salivary glands) as well as hNIS-transfected tissues. Thus, non-invasive PET imaging of hNIS activity could be used to facilitate the treatment of thyroid and breast cancer and gene therapies that employ hNIS as a reporter gene. In principle, the $^{18}$F-TFB PET method may also enable quantitative estimation of hNIS activity in tissues. Therefore, it may be useful to monitor changes over time for understanding the progression of disease and serial assessments of therapy response.

Since only high specific radioactivity $^{18}$F-TFB was administered in this study, we did not explore the effects of specific radioactivity over a broader range. However, in our previous preclinical study with NIS-transfected C6 glioma xenografts in mice we showed that as specific radioactivity was decreased such that TFB administration levels exceeded ~0.5 mg/kg, there was decreases seen in both thyroid and tumor uptake. Since thyroid uptake levels in the healthy participants in this study were very high, it is inferred that the specific radioactivity levels were sufficient to avoid any saturation effects do to administered TFB mass.

The regional distribution of $^{18}$F-TFB in healthy participants was found to be consistent with known hNIS expression levels throughout the body tissues. The slow accumulation of $^{18}$F-radioactivity seen in SUV values between the 2 and 3.5 h imaging time points could be evidence of a minor degree of radiotracer defluorination, but since routine $^{18}$F-TFB PET images will likely be acquired in the 1-2 h post-injection period, the impact of this accumulation is of minor significance. Indeed, bone uptake was not qualitatively remarkable in either the 2 or 3.5 h images. Overall, the biodistribution data confirm $^{18}$F-TFB to be an excellent iodide analog radiotracer with excellent in vivo stability.

The estimated radiation doses were higher in thyroid, urinary bladder wall, lower large Intestine wall, small intestine wall, upper large intestine wall, heart wall, kidneys, liver, pancreas, and spleen, but on par with other $^{18}$F-labeled radiopharmaceuticals and appropriate for clinical use. Further decrease in bladder wall doses can be realized with good hydration and more frequent voiding of the bladder. Estimated effective doses were 0.036 mSv/MBq in males and 0.064 mSv/MBq in females. Our data on the biodistribution and dosimetry estimates for $^{18}$F-TFB are in general agreement with the results very recently published O'Doherty et al. (11) in five patients with thyroid cancer. In that study, 2 male and 3 female subjects were studied and the results from both genders were pooled. The specific radioactivity of their $^{18}$F-TFB preparations (24±13 MBq/µg) was similar to the specific radioactivity obtained in this study.

Conclusion

The pharmacokinetics and biodistribution of high-specific activity $^{18}$F-TFB in healthy human participants support its use as an iodide analog radiotracer for evaluation of thyroid and breast cancers and monitoring of gene therapies that employ the hNIS reporter gene. The radiation dosimetry estimates are on par with other $^{8}$F-labeled radiopharmaceuticals with prominent renal excretion (e.g. $^{18}$F-FDG) and are acceptable for clinical imaging purposes.

REFERENCES FROM EXAMPLE 2

1. Chung J K. Sodium iodide symporter: Its role in nuclear medicine. *J Nucl Med* 2002; 43:1188-1200.

2. Penheiter A R, Russell S J, and Carlson S K. The sodium iodide symporter (NIS) as an imaging reporter for gene, viral, and cell-based therapies. *Curr Gene Ther.* 2012; 12:33-47.
3. Ahn B-C. Sodium Iodide Symporter for Nuclear Molecular Imaging and Gene Therapy: From Bedside to Bench and Back. *Theranostics.* 2012; 2:392-402.
4. Dai O, Levy O, and Carrasco N. Cloning and characterization of the thyroid iodide transporter. *Nature.* 1996; 379:458-460.
5. Eskandari S, Loo D D F, Dai G, Levy O, Wright E M, and Carrasco N. Thyroid Na+/I− Symporter Mechanism, Stoichiometry, and Specificity. *J Biol Chem.* 1997; 272: 27230-27238.
6. Miller A and Russell S J. The use of the NIS reporter gene for optimizing oncolytic virotherapy. *Expert Opin on Biol Ther.* 2016; 16:15-32.
7. Jauregui-Osoro M, Sunassee K, Weeks A J, Berry D J, Paul R L, Cleij M, et al. Synthesis and biological evaluation of F-18 tetrafluoroborate: a PET imaging agent for thyroid disease and reporter gene imaging of the sodium/iodide symporter. *Eur J Nucl Med Mol Imaging.* 2010; 37:2108-2116.
8. Weeks A J, Jauregui-Osoro M, Cleij M, Blower J E, Ballinger J R, and Blower P J. Evaluation of F-18-tetrafluoroborate as a potential PET imaging agent for the human sodium/iodide symporter in a new colon carcinoma cell line, HCT16, expressing hNIS. *Nucl Med Comm.* 2011; 32:98-105.
9. Marti-Climent J M, Collantes M, Jauregui-Osoro M, Quincoces G, Prieto E, Bilbao I, et al. Radiation dosimetry and biodistribution in non-human primates of the sodium/iodide PET ligand F-18-tetrafluoroborate. *EJNMMI Research.* 2015; 5:70.
10. Youn H, Jeong J M, and Chung J-K. A new PET probe, F-18-tetrafluoroborate, for the sodium/iodide symporter: possible impacts on nuclear medicine. *Eur J Nucl Med Mol Imaging.* 2010; 37:2105-2107.
11. O'Doherty J, Jauregui-Osoro M, Brothwood T, Szyszko T, Marsden P, O'Doherty M, Cook G, Blower P, Lewington V. $^{18}$F-tetrafluoroborate ($^{18}$F-TFB), a PET probe for imaging sodium-iodide symporter expression: Whole-body biodistribution, safety and radiation dosimetry in thyroid cancer patients. *J Nucl Med.* 2017 pii: jnumed.117.192252. doi: 10.2967/jnumed.117.192252. [Epub ahead of print]
12. Jiang H L, Bansal A, Pandey M K, Peng K W, Suksanpaisan L, Russell S J, et al. Synthesis of F-18-Tetrafluoroborate via Radiofluorination of Boron Trifluoride and Evaluation in a Murine C6-Glioma Tumor Model. *J Nucl Med* 2016; 57:1454-1459.
13. Khoshnevisan A, Jauregui-Osoro M, Shaw K, Torres J B, Young J D, Ramakrishnan N K, et al. F-18 tetrafluoroborate as a PET tracer for the sodium/iodide symporter: the importance of specific activity. *EJNMMI Research.* 2016; 6:34.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto.

The invention claimed is:

1. A method of radiolabeling tetrafluoroborate (TFB) with $^{18}$F-fluoride, the method comprising:
    (a) trapping $^{18}$F-fluoride on an anion exchange column;
    (b) reacting $^{18}$F-fluoride with boron trifluoride (BF$_3$); and
    (c) isolating the $^{18}$F-TFB from unreacted $^{18}$F-fluoride and BF$_3$ from the anion exchange column, wherein the resultant $^{18}$F-TFB has a specific activity of at least 5 GBq/µmol.

2. The method of claim 1, wherein the BF$_3$ in step (b) is provided in a solution of boron trifluoride-tetrahydrofuran (BF$_3$-THF) complex in petroleum ether.

3. The method of claim 2, wherein BF$_3$-THF complex is filtered to remove TFB before reacting with $^{18}$F-fluoride.

4. The method of claim 1, wherein the column is washed after step (b) to remove unreacted BF$_3$ and residual solvent from the column.

5. The method of claim 1, wherein the $^{18}$F-TFB has a specific activity of at least 8 GBq/µmol.

6. The method of claim 1, wherein the $^{18}$F-TFB is synthesized in radiochemical yield of 15% with greater than 95% radiochemical purity.

7. The method of claim 1, wherein the $^{18}$F-TFB is synthesized in radiochemical yield of 20% with greater than 95% radiochemical purity.

8. The method of claim 1, wherein the method consists essentially of steps (a), (b), and (c).

9. The method of claim 1, wherein the anion exchange column is a quaternary methyl ammonium anion exchange (QMA) cartridge.

* * * * *